(12) United States Patent
Konstantinova et al.

(10) Patent No.: US 10,383,858 B2
(45) Date of Patent: *Aug. 20, 2019

(54) PPAR COMPOUNDS FOR USE IN THE TREATMENT OF FIBROTIC DISEASES

(71) Applicant: INVENTIVA, Daix (FR)

(72) Inventors: Irena Konstantinova, Talant (FR); Jean-Michel Luccarini, Dijon (FR); Jean-Louis Junien, Sevres (FR); Pierre Broqua, Antony (FR)

(73) Assignee: INVENTIVA, Daix (FR)

( * ) Notice: Subject to any disclaimer, the term of this patent is extended or adjusted under 35 U.S.C. 154(b) by 0 days.

This patent is subject to a terminal disclaimer.

(21) Appl. No.: 16/043,976

(22) Filed: Jul. 24, 2018

(65) Prior Publication Data

US 2018/0333396 A1   Nov. 22, 2018

Related U.S. Application Data

(63) Continuation of application No. 15/318,553, filed as application No. PCT/EP2015/063196 on Jun. 12, 2015, now Pat. No. 10,052,311.

(30) Foreign Application Priority Data

| Jun. 13, 2014 | (EP) | 14305894 |
| Jun. 13, 2014 | (EP) | 14305895 |
| Jun. 13, 2014 | (EP) | 14305896 |
| Jun. 13, 2014 | (EP) | 14305897 |
| Dec. 24, 2014 | (EP) | 14307187 |

(51) Int. Cl.
A61K 31/428 (2006.01)

(52) U.S. Cl.
CPC .................. A61K 31/428 (2013.01)

(58) Field of Classification Search
CPC .................................................. A61K 31/428
USPC ........................................................ 514/367
See application file for complete search history.

(56) References Cited

U.S. PATENT DOCUMENTS

| 2010/0286137 A1 | 11/2010 | Binet et al. |
| 2013/0108573 A1 | 5/2013 | Gedulin et al. |
| 2013/0287794 A1 | 10/2013 | Radstake |
| 2014/0038956 A1 | 2/2014 | Hirth-Dietrich et al. |

FOREIGN PATENT DOCUMENTS

| FR | 2890071 | 3/2007 |
| JP | 2007191424 | 8/2007 |
| WO | 2004103296 | 12/2004 |
| WO | 2007026097 | 3/2007 |
| WO | 2007030559 | 3/2007 |
| WO | 2009149188 | 12/2009 |
| WO | 2011064350 | 6/2011 |
| WO | 2012159107 | 11/2012 |
| WO | 2013071077 | 5/2013 |
| WO | 2014013005 | 1/2014 |

OTHER PUBLICATIONS

Gamble et al., J. Zoo. Wildl. Med. (2004); 35(3), pp. 361-369.
Raja Vuppalanchi et al.: "Nonalcoholic Fatty Liver Disease and Nonalcoholic Steatohepatitis: Selected Practical Issues in Their Evaluation and Management"; Hepatology, 2009, vol. 49, No. 1, pp. 306-317.
J. K. Dowman et al.: "Pathogenesis of non-alcoholic fatty liver disease"; Q. J. Med, 2010, vol. 103, pp. 71-83.
Neuschwander-Tetri et al.: "Improved Nonalcoholic Steatohepatitis After 48 Weeks of Treatment With the PPAR-y Ligand Rosiglitazone"; Hepatology, 2003, Vo. 38, No. 4, pp. 1008-1017.
Nelson et al: "A Pilot Study Using Simvastatin in the Treatment of Nonalcoholic Steatohepatitis"; J. Clin. Gastroenterol, 2009, vol. 43, pp. 990-994.
J. Kung et al: "Thiazolidinedione safety"; Expert Opinion on Drug Safety, 2012, vol. 11, pp. 565-579.
Lakota et al.: "Levels of adiponectin, a marker for PPAR-gamma activity, correlate with skin fibrosis in systemic sclerosis: potential utility as biomarker?"; Arthritis Research & Therapy, 2012, pp. 2-6.
Bogatkevich et al.: "The PPARγ Agonist Rosiglitazone is Antifibrotic for Scleroderma Lung Fibroblasts: Mechanisms of Action and Differential Racial Effects"; Pulmonary Medicine, 2012, Vo. 2012, pp. 1-9.
Aoki et al.: "Pioglitazone, a Peroxisome Proliferator-Activated Receptor Gamma Ligand, Suppresses Bleomycin-Induced Acute Lung Injury and Fibrosis"; Respiration, Basic Science Investigations, 2009, vol. 77, pp. 311-319.
Samah et al.: "Evaluation of the antifibrotic effect of fenofibrate and rosiglitazone on bleomycin induced pulmonary fibrosis in rats"; European Journal of Pharmacology, 2012, pp. 186-193.
Galuppo et al.: "GW0742, A High Affinity PPAR-pto Agonist Reduces Lung Inflammation Induced by Bleomycin Instillation in Mice"; International Journal of Immunopathology and Pharmacology, 2010, vol. 23, pp. 1033-1046.
Shiri-Sverdlov et al.: "Early diet-induced non-alcoholic steatohepatitis in APOE2 knock-in mice and its prevention by fibrates"; Journal of Hepatology, 2006, vol. 44, pp. 732-741.
Yao et al: "Inhibition of carbon tetrachloride-induced liver injury by liposomes containing vitamin E"; American Physiological Society, 1994, pp. G476-G484.
Livak et al.: "Analysis of Relative Gene Expression Data Using Real-Time Quantitative PCR and the 2-ΔΔCT Method"; Methods, vol. 25, 2001, pp. 402-408.
Corbel et al: "Modulation of airway remodeling-associated mediators by the antifibrotic compound, pirfenidone, and the matrix metalloproteinase inhibitor, batimastat, during acute lung injury in mice" European Journal of Pharmacology, 2001, vol. 426, pp. 113-121.
Manoury et al.: "TIMP-I is a Key Factor of Fibrogenic Response to Bleomycin in Mouse Lung"; International Journal of Immunopathology and Pharmacology, 2006, vol. 19, pp. 471-487.

(Continued)

*Primary Examiner* — Taofiq A Solola
(74) *Attorney, Agent, or Firm* — Hamre, Schumann, Mueller & Larson, P.C.

(57) ABSTRACT

The invention relates to the use of a pan-PPAR agonist, or of a pharmaceutical composition containing said agonist, for the treatment of a fibrotic condition.

10 Claims, 20 Drawing Sheets
Specification includes a Sequence Listing.

(56) References Cited

OTHER PUBLICATIONS

A. Benardeau et al: "Effects of the dual PPAR-α/γ agonist aleglitazar on glycaemic control and organ protection in the zucker diabetic fatty rat" Diabetes, Obesity and Metabolism, vol. 15, 2012, pp. 164-174.

B. Steals et al.: Hepatoprotective Effects of the Dual Peroxisme Proliferator-Activated Receptor Alpha/Delta Agonist, GFT505, in Rodent Models of Nonalcoholic Fatty Liver Disease/Nonalcoholic Steatohepatitis, Hepatology, vol. 58, No. 6, 2013, pp. 1941-1952.

International Search Report issued in International Application No. PCT/EP2015/063196 dated Oct. 8, 2015 (5 pages).

Written Opinion issued in International Application No. PCT/EP2015/063196 dated Oct. 8, 2015 (5 pages).

Lakatos, H. F. et al., "The Role PPARs in Lung Fibrosis," PPAR Research, Hindawi Publishing Corporation, vol. 2007, Article ID 71323, pp. 1-10.

Nakano, S. et al., "Bezafibrate prevents hepatic stellate cell activation and fibrogenesis in a murine steatohepatitis model, and suppresses fibrogenic response induced by transforming growth factor-β1 in a cultured stellate cell line," Hepatology Research, 2008, 38, pp. 1026-1039.

Tenenbaum, A. et al., "Balanced pan-PPAR activator bezafibrate in combination with statin: comprehensive lipids control and diabetes prevention?" Cardiovascular Diebetology, 2012, 11:140, 9 pages.

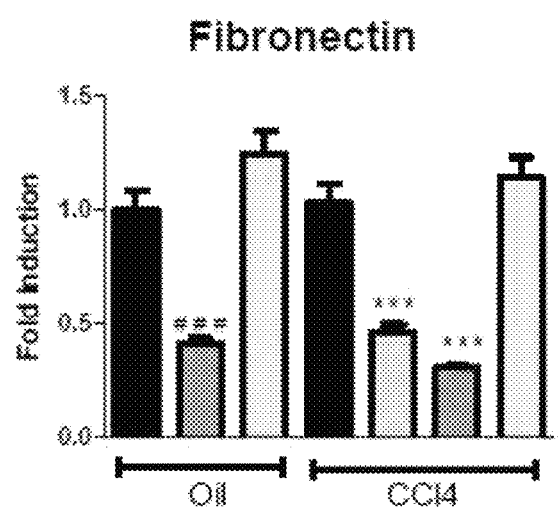
FIG. 7
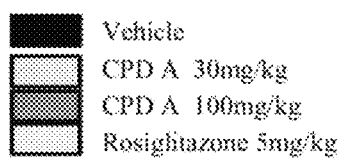
Vehicle
CPD A 30mg/kg
CPD A 100mg/kg
Rosiglitazone 5mg/kg
Legend to figures 1 to 7

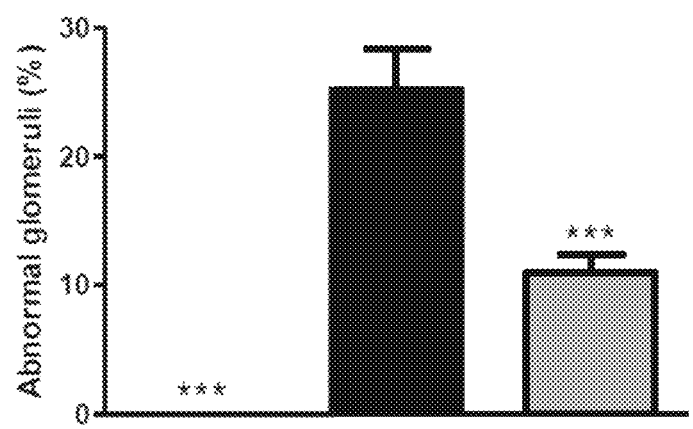
FIG. 16
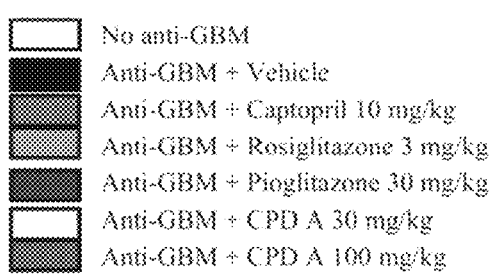
- No anti-GBM
- Anti-GBM + Vehicle
- Anti-GBM + Captopril 10 mg/kg
- Anti-GBM + Rosiglitazone 3 mg/kg
- Anti-GBM + Pioglitazone 30 mg/kg
- Anti-GBM + CPD A 30 mg/kg
- Anti-GBM + CPD A 100 mg/kg
Legend to figures 8 to 16

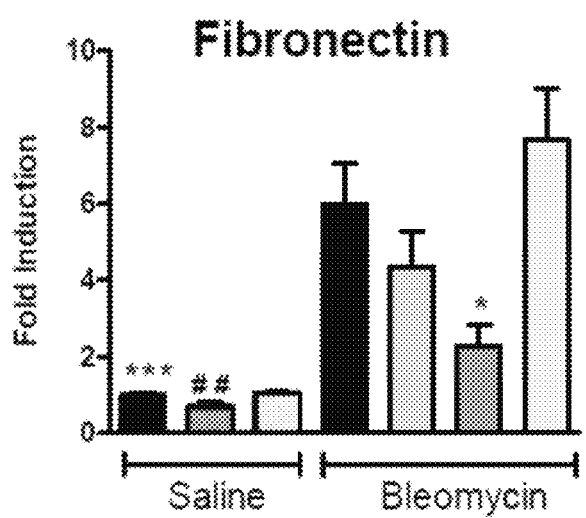
FIG. 27
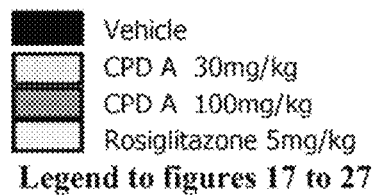
Legend to figures 17 to 27

PPAR COMPOUNDS FOR USE IN THE TREATMENT OF FIBROTIC DISEASES

FIELD OF THE INVENTION

The present invention relates to the use of a pan-PPAR agonist or of a pharmaceutical compositors containing said agonist, for the treatment of fibrotic diseases.

BACKGROUND OF THE INVENTION

Liver fibrosis is the result of a complex interplay among different cell types. It is characterized by the recruitment of inflammatory cells in response to chronic injury and by the activation of hepatic stellate cells (HSCs), leading to the accumulation of extracellular matrix. Steatosis is commonly coexisting with hepatic inflammation and hepatocellular injury. Increased oxidative stress is a common factor in all chronic liver diseases leading to fibrosis, regardless of their etiology. Injured hepatocytes, HSCs, and infiltrating inflammatory cells are major sources of reactive oxygen species (ROS). Indeed, the oxidative stress will induce the recruitment of inflammatory cells and the activation of HSCs. Therefore, in a chronic liver injury context, a vicious circle of hepatocyte damage, ROS production, HSC activation, and inflammatory cell recruitment will occur, amplifying the fibrogenic answer to injury.

Means for an effective treatment for liver fibrotic diseases, such as non-alcoholic fatty liver disease (NAFLD) and non-alcoholic steatohepatitis (NASH), are still insufficient. No treatment is established for patient with NASH, and several therapeutic options are tested in clinical trial (Vuppalanchi R and Chalasani N, Hepatology 2009, 49(1): 306-317; Dowman J. K et al., Q. J. Med. 2010, 103(2):71-83). These studies involve the use of many different families of chemical compounds (fibrates, thiazolidinediones, biguanides, statins, cannabinoids) and therapeutic targets (nuclear receptors, angiotensin receptors, cannabinoid receptors, HMG-CoA reductase). Recently, studies involving thiazolidinediones (rosiglitazone and pioglitazone) have shown that these drugs may improve liver condition but treatment with these drugs is not without undesired effects such as higher risks of congestive cardiac failure and osteoporosis, as well as weight gain with psychological effects on the patient (Dowman J. K et al., op. cit.; Shiri-Sverdlov R et al., J. Hepatol. 2006 44: 732-41; Neuschwander-Tetri et al., Hepatology 2003, 38:1008-1017). Clinical trials involving the administration of cannabinoids have raised the concern of neuropsychiatric disruption (Vuppalanchi R and Chalasam N, op. cit.). Other therapies currently ongoing are seeking to assess in NASH drugs as antioxidants but none of these treatments has yet showed convincing results (Nelson A et al., J. Clin. Gastroenterol 2009, 43: 990-994). Candidates for the treatment of liver diseases are disclosed in WO 2011/064350 and US 2013/108573. There is still a need, however, for compounds which are suitable for the treatment of liver diseases, in particular for compounds which may target the several components of fibrotic process such as steatosis, inflammation and collagen deposition and are devoid of the side effects observed with the drugs currently under evaluation.

Chronic kidney disease (CKD), also known as chronic renal disease, is a progressive loss in renal function over a period of months or years. CKD has its general meaning in the art and is used to classify numerous conditions that affect the kidney, destruction of the renal parenchyma and the loss of functional nephrons or glomeruli. It should be further noted that CKD can result from different causes, but the final pathway remains renal fibrosis. Examples of etiology of CKD include, but are not limited to, cardiovascular diseases, hypertension, diabetes, glomerulonephritis, polycystic kidney diseases, and kidney graft rejection. Renal fibrosis, characterized by glomerulosclerosis and tubuloininterstitial fibrosis, is the common manifestation of a wide variety of chronic kidney diseases. The pathogenesis of renal fibrosis is, in essence, a monotonous process that is characterized by an excessive accumulation and deposition of extracellular matrix (ECM) components. Renal fibrosis is a progressive process that ultimately leads to end-stage renal failure, a devastating disorder that requires dialysis or kidney transplantation. However, there is no specific treatment unequivocally shown to slow the worsening of chronic kidney disease. Injury to the kidney is associated with release of cytokines/growth factors such as TGF-β, epidermal growth factor (EGF), and platelet derived growth factor (PDGF) by damaged or infiltrating cells. An increase in production of TGF-β is one of the most important mechanisms in the pathogenesis of renal fibrogenesis. TGF-β1 stimulates fibroblast cell activation and induces matrix expression through its interaction with TGF-β receptors, which are mainly composed of two protein families—type I (TβRI) and type II (TβRII) receptors. TGF-β1 binds to TβRII, which results in TβRI recruitment to form a heteromeric TGF-β receptor complex. The complex phosphorylates and activates Smad2 and Smad3, the two major Smads that mediate the profibrotic events. Other signaling pathways such as extracellular regulated kinase 1/2 (ERK1/2) can also be activated in response to TGF-β receptor activation. Activated ERK1/2 contributes to tubular cell apopiosis in the obstructive kidney. Since actuation of TCP-β signaling is considered to be the major mechanism that directly promotes fibroblast activation and fibrosis progression, therapeutic intervention of this pathway could be considered as a strategy to halt or prevent renal fibrosis. Candidates for the treatment of CKD are disclosed in WO 2012/159107 and WO 2014/013005. There is still a need, however, for compounds which are suitable for the treatment of CKD.

Lung fibrotic remodelling occurs in pulmonary disease conditions such as acute respiratory distress syndrome, chronic obstructive pulmonary disease and asthma. Pulmonary fibrosis is characterised by the excessive deposition of extracellular matrix in the interstitium, resulting in respiratory failure. Pulmonary fibrosis can be caused by a number of different conditions, including sarcoidosis, hypersensitivity pneumonitis, collagen vascular disease, and inhalant exposure. In a significant number of patients, no underlying cause for the pulmonary fibrosis can be found. These conditions of unknown etiology have been termed idiopathic interstitial pneumonias. The most common form of idiopathic interstitial pneumonia is idiopathic pulmonary fibrosis (IPF). The primary histopathologic finding of IPF is that of usual interstitial pneumonia with temporal heterogeneity of alternating zones of interstitial fibrosis with fibroblastic foci (i.e., newer fibrosis), inflammation, honeycomb changes (i.e., older fibrosis), and normal lung architecture (i. e., no evidence of fibrosis). Candidates for the treatment of IPF are disclosed in WO 2004/103296. Candidates for the treatment of pulmonary fibrotic disorders are disclosed in WO 2009/149188. Recently, studies involving thiazolidinediones such as rosiglitazone have shown that these drugs may improve pulmonary fibrosis but treatment with these drugs is not without undesired effects such as higher risks of congestive cardiac failure (Kung J et al., Expert Opin. Drug Saf. 2012, 11(4):565-579). Pirfenidone (5-methyl-1-phenyl-2-(1H)- pyridone) has anti-fibrotic properties and is approved in Europe and Japan for the treatment of IPF. There is still a need, however, for alternative compounds which are suitable for the treatment of pulmonary fibrotic disorders.

Fibrotic disorders are characterized by abnormal and excessive deposition of collagen and other extracellular matrix (ECM) components in various tissues. Although their aetiology is quite diverse, the presence of ECM-producing fibroblasts displaying an activated phenotype in the affected tissues is typical of fibrotic diseases. Fibroblast activation is characterized by a marked increase in the transcriptional activity of the genes encoding type I and type III collagens and fibronectin, initiation of the expression of alpha-smooth muscle actin (α-SMA), and the reduction of ECM degradative activities. The most frequent systemic fibrotic disorder is systemic fibrosis which is a rate chronic disease of unknown cause. It is a clinically heterogeneous, systemic disorder which affects the connective tissue of the skin internal organs and the walls of blood vessels. It is characterized by alterations of the microvasculature, disturbances of the immune system and by massive deposition of collagen and other matrix substances in the connective tissue. Basic functions of various cell types (endothelial cells, T-lymphocytes, monocytes, fibroblasts, mast cells) as well as the production and effects of cytokines, growth factors, and adhesion molecules are known to be involved in the development of this disease. Systemic fibrosis is often referred to as scleroderma. The spectrum of sclerodermatous diseases comprises a wide variety of clinical entities such as morphea (patchy, linear, and generalized), pseudo-scleroderma and the overlap-syndromes with similar cutaneous and histopathologic manifestations. In addition, the complex pathophysiology of systemic fibrosis, involving genetic factors, environmental factors, vascular and immune system functions, as well as fibroblasts and matrix substances, and the complexity of the internal organ involvement, results in sclerodermatous diseases often being studied as autoimmune or connective tissue diseases. Therefore, systemic fibrosis has been a challenge for clinicians with regards to diagnostic procedures and therapeutic regimens. Clinical diagnosis of systemic fibrosis often involves attention from several disciplines (e.g. dermatologists, rheumatologists, pulmonologists, nephrologists, and gastroenterologists) and may include invasive procedure such as a biopsy of the fibrotic tissue and/or skin for confirmation. Candidates for the treatment of systemic fibrosis are disclosed in US 2013/0287794 and US 2014/0038956. There is still a need however, for alternative compounds which are suitable for the treatment of systemic fibrosis.

The peroxisome proliferator-activated receptors (PPARs) are a group of nuclear receptor proteins that function as transcription factors regulating the expression of genes. PPARs play essential roles in the regulation of cellular differentiation, development, and metabolism (carbohydrate, lipid, protein). Three subtypes of PPARs have been identified:

PPARα, which are mainly expressed in liver, kidney, heart, muscle, adipose tissue and lungs;
PPARγ, which are expressed in virtually all tissues;
PPARδ, which are observed on a variety of tissues/cells notably in the cardiovascular, urinary, respiratory, digestive and musculoskeletal systems.

PPAR agonists are drugs which act upon the PPARs. They are used for the treatment of symptoms of the metabolic diseases, mainly for lowering triglycerides and blood sugar. PPARα agonists essentially consist of the class of fibrates (e.g. fenofibrate). PPARγ agonists essentially consist of thiazolidinediones (e.g. rosiglitazone and pioglitazone). PPARδ agonists include GW501516, a candidate compound that was eventually discontinued due to safety issues.

PPAR receptors expression is modified in fibrosis diseases. For example, decrease expression of PPARγ has been reproducibly described in skin biopsies, as well as in explanted skin fibroblasts from systemic scleroderma patients (Lakota et al, Arthritis Res. Ther. 2012 May 1; 14(3)). A lower expression of PPARγ was also reported in lung fibroblasts from scleroderma patients (Bogatkevich et al, Pulm. Med. Vol 2012; 2012). PPARγ agonists rosiglitazone and pioglitazone protect rodents from bleomycin-induced skin and lung fibrosis in vivo and prevent activation of profibrolic pathways and processes in vitro in fibroblast cell lines and in primary fibroblasts (Aoki et al, Respiration. 2009:77(3):311-9; Samah et al, Eur J Pharmacol. 2012 Aug. 15; 689(1-3)). PPARα receptors also modulate the profibrolic response to different stimuli. In the lung, fenofibrate, a specific PPARα agonist, prevented bleomycin-induced fibrosis (Samah et al 2012 op cit). Furthermore, PPARδ agonist GW0742 has been shown to reduce lung inflammation induced by bleomycin instillation in mice (Galuppo et al. Int J Immunopathol Pharmacol. 2010 October-December; 23(4):1033-46).

SUMMARY OF THE INVENTION

It has now been found that pan-PPAR agonists, i.e. compounds which activate all three PPAR receptors (PPARα, PPARγ and PPARδ), exert beneficial effects in the treatment of various fibrotic conditions. The present invention therefore provides a pan-PPAR agonist for use in a method of treatment of a fibrotic condition. The invention also provides compositions and methods for treating a fibrotic condition.

In one embodiment, the fibrotic condition is a condition affecting any organ which can develop fibrosis, such as the heart, the lung, the liver, the kidney, the gastrointestinal tract, the skin, etc.

In another embodiment, the fibrotic condition is selected from: liver fibrosis, fatty liver disease, non-alcoholic steatohepatitis, chronic kidney disease, a pulmonary fibrotic disorder such as idiopathic pulmonary fibrosis, and systemic scleroderma.

In yet another embodiment, which can be combined with the previous ones, the pan-PPAR agonist is intended tor oral administration.

BRIEF DESCRIPTION OF THE DRAWINGS

FIG. 7 shows Fibronectin expression in $CCl_4$-exposed mice treated with vehicle, compound A and rosiglitazone.

Legend to FIGS. 1 to 7: in the oil group the bars represent, from left to right, vehicle, compound A (100 mg/kg) and rosiglitazone, in the CCl$_4$ group the bars represent, from left to right, vehicle compound A (30 mg/kg) compound A (100 mg/kg) and rosiglitazone.

Figure 8:
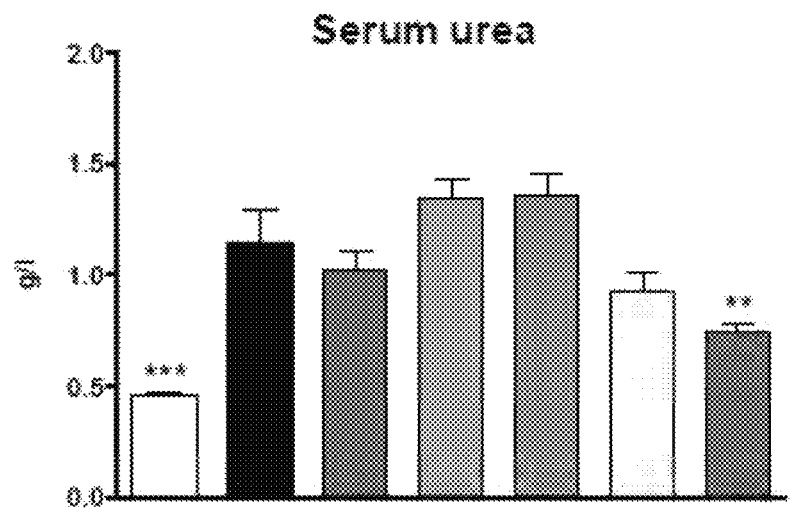

FIG. 8 shows serum urea levels of anti-GBM exposed mice treated with vehicle, captopril, rosiglitazone, pioglitazone and compound A.

Figure 9:
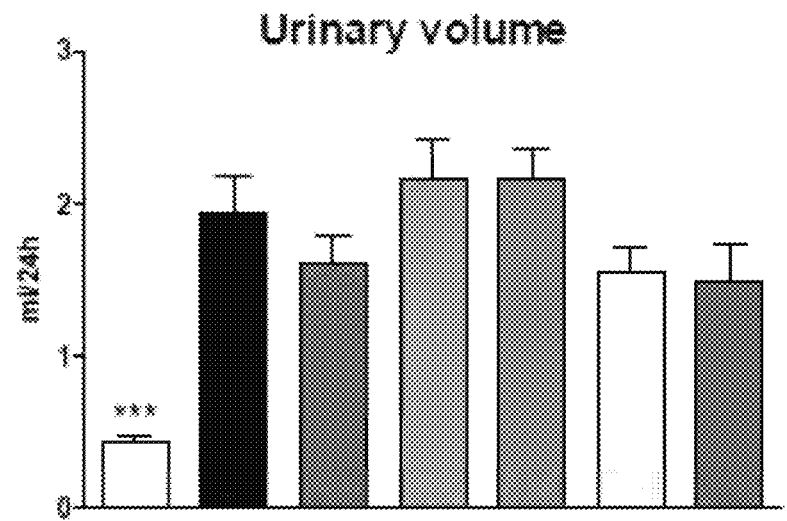

FIG. 9 shows urinary volumes of anti-GBM exposed mice treated with vehicle, captopril, rosiglitazone, pioglitazone and compound A.

Figure 10:
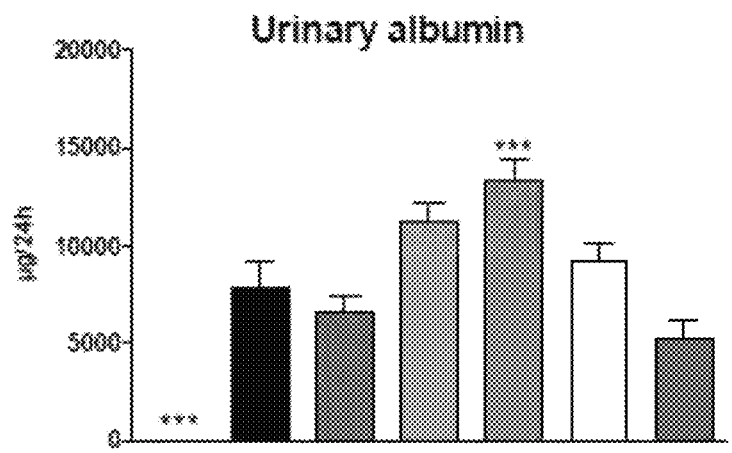

FIG. 10 shows urinary albumin levels of anti-GBM exposed mice treated with vehicle, captopril, rosiglitazone, pioglitazone and compound A.

Figure 11:
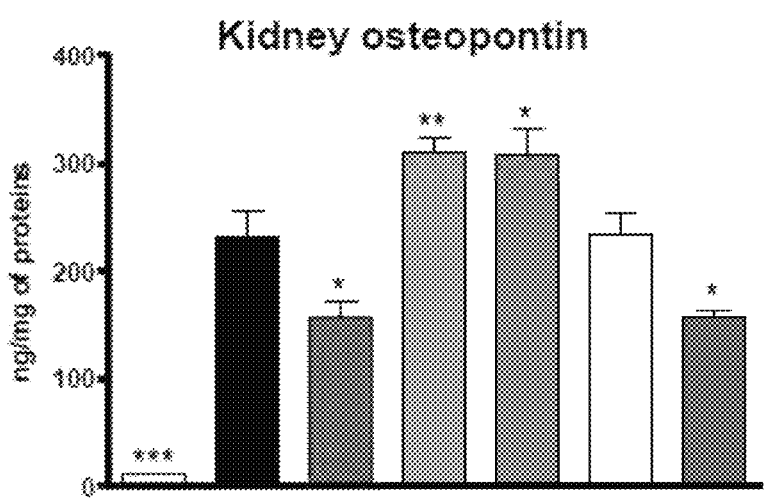

FIG. 11 shows osteopontin levels of anti-GBM exposed mice treated with vehicle, captopril, rosiglitazone, pioglitazone and compound A.

Figure 12:
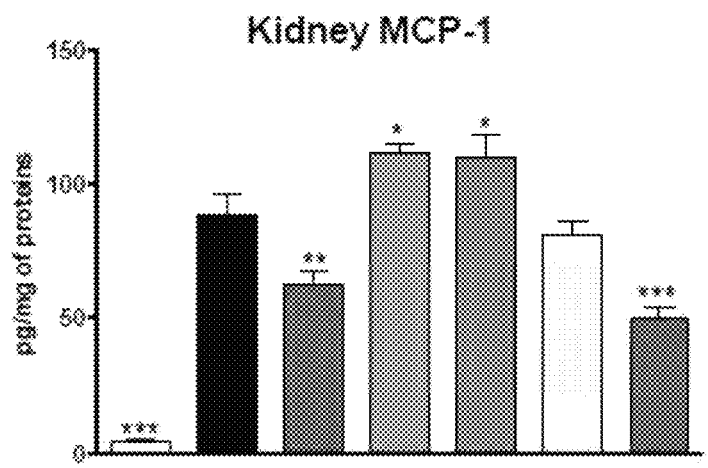

FIG. 12 shows MCP-1 levels of anti-GBM exposed mice treated with vehicle, captopril, rosiglitazone, pioglitazone and compound A.

Figure 13:
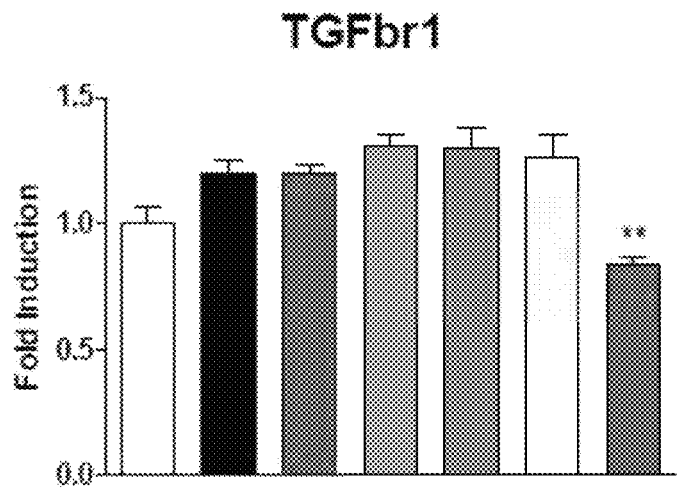

FIG. 13 shows TGFβR1 expression, of anti-GBM exposed mice treated with vehicle, captopril, rosiglitazone, pioglitazone and compound A.

Figure 14:
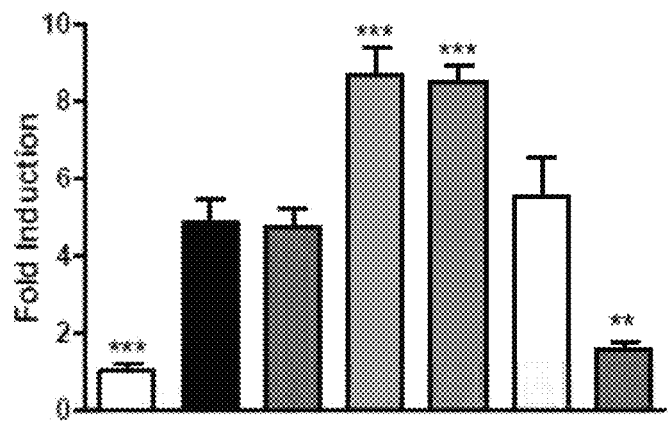

FIG. 14 shows Col1a expression of anti-GBM exposed mice treated with vehicle, captopril, rosiglitazone, pioglitazone and compound A.

Figure 15:
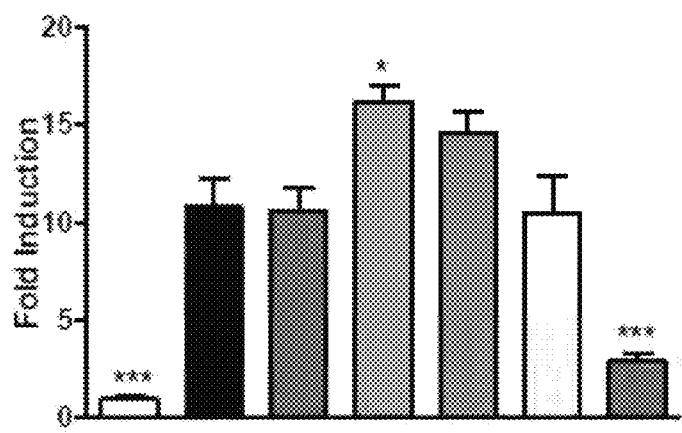

FIG. 15 shows Col3a expression of anti-GBM exposed mice treated with vehicle, captopril rosiglitazone, pioglitazone and compound A.

FIG. 16 shows the number of pathologies glomeruli in anti-GBM exposed mice treated with vehicle and compound A.

Legend to FIGS. 8 to 15: the bars represent, from left to right, control mice, anti-GBM exposed mice treated with vehicle, anti-GBM exposed mice treated with captopril anti-GBM exposed mice treated with rosiglitazone, anti-GBM exposed mice treated with pioglitazone, anti-GBM exposed mice treated with compound A (30 mg/kg) and anti-GBM exposed mice treated with compound A (100 mg/kg). Legend to FIG. 16: the bars represent, from left to right, anti-GBM exposed mice treated with vehicle and anti-GBM exposed mice treated with compound A (100 mg/kg).

Figure 17:
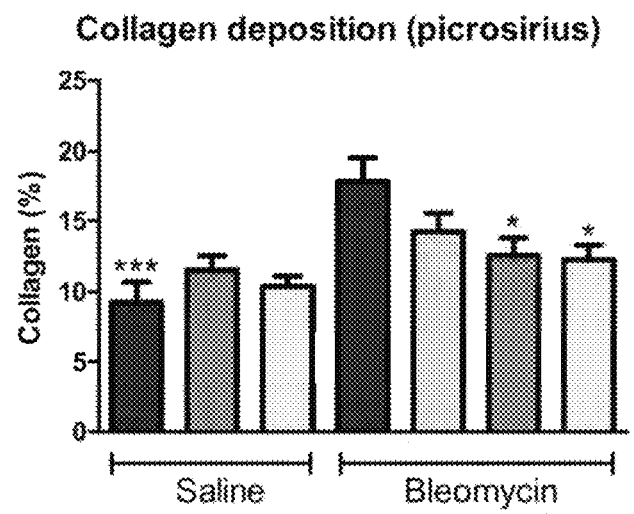

FIG. 17 shows collagen deposition in bleomycin-exposed mice treated with vehicle, compound A and rosiglitazone.

Figure 18:
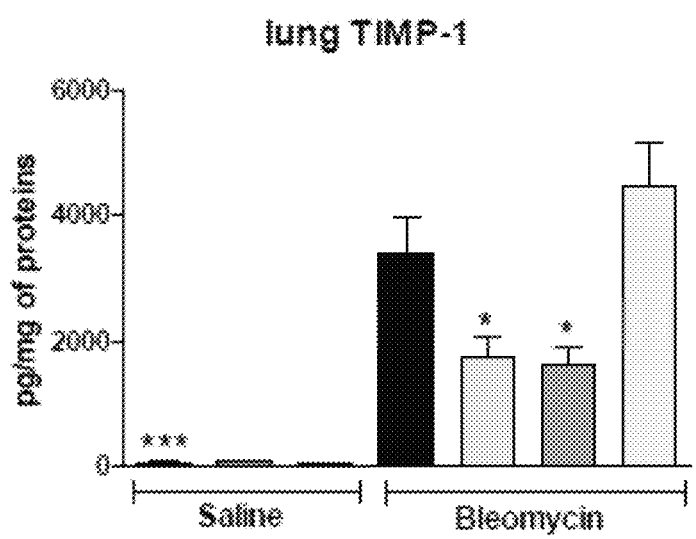

FIG. 18 shows TIMP-1 levels in bleomycin-exposed mice treated with vehicle, compound A and rosiglitazone.

Figure 19:
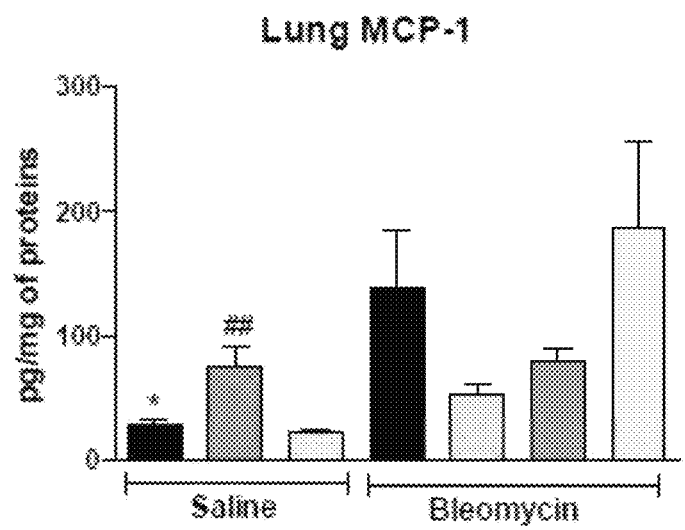

FIG. 19 shows MCP-1 levels in bleomycin-exposed. mice treated with vehicle, compound A and rosiglitazone.

Figure 20:
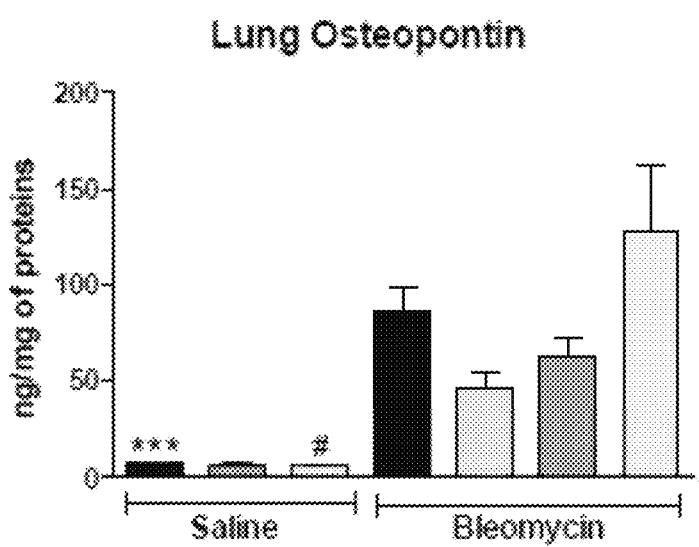

FIG. 20 shows osteopontin levels in bleomycin-exposed mice treated with vehicle, compound A and rosiglitazone.

Figure 21:
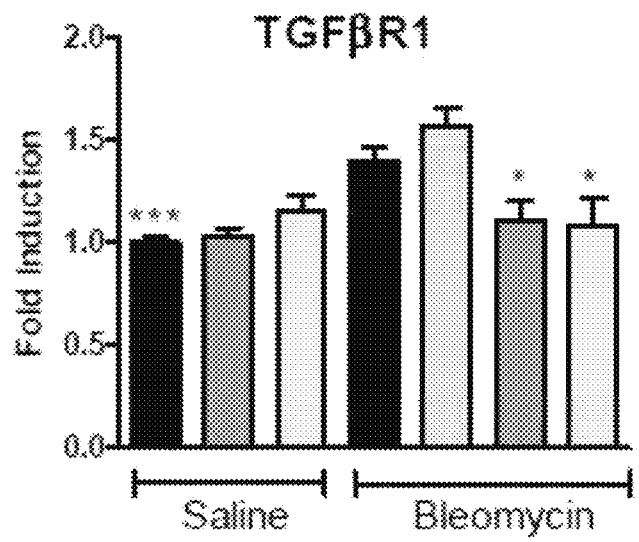

FIG. 21 shows TGFβR1 expression in bleomycin-exposed mice treated with vehicle, compound A and rosiglitazone.

Figure 22:
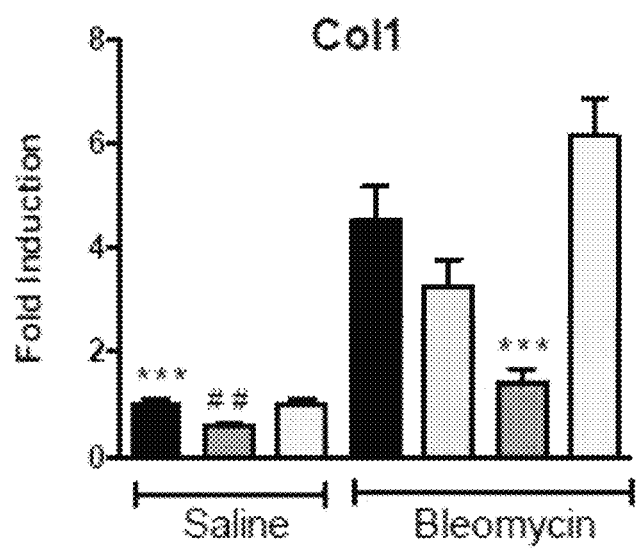

FIG. 22 shows Col1a expression in bleomycin-exposed mice treated with vehicle, compound A and rosiglitazone.

Figure 23:
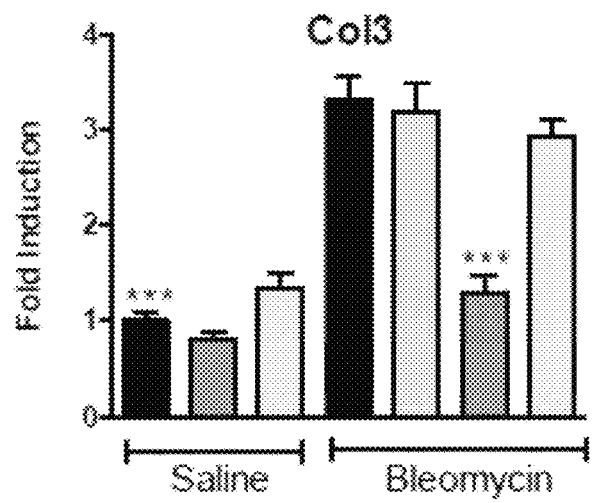

FIG. 23 shows Col3a expression in bleomycin-exposed mice treated with vehicle, compound A and rosiglitazone.

Figure 24:
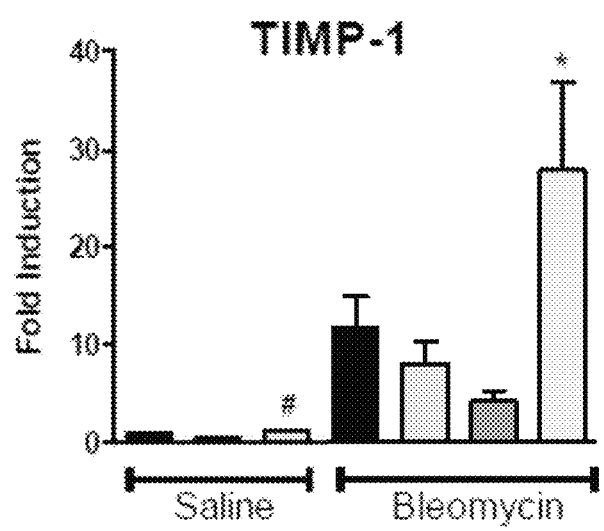

FIG. 24 shows TIMP-1 expression in bleomycin-exposed mice treated with vehicle, compound A and rosiglitazone.

Figure 25:
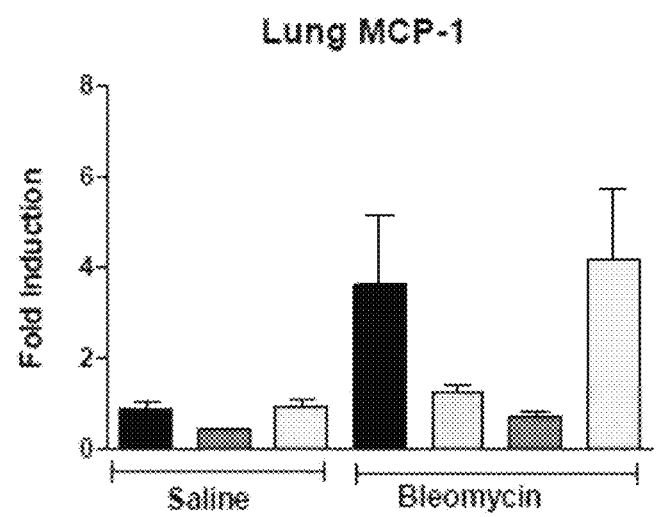

FIG. 25 shows MCP-1 expression in bleomycin-exposed mice treated with vehicle, compound A and rosiglitazone.

Figure 26:
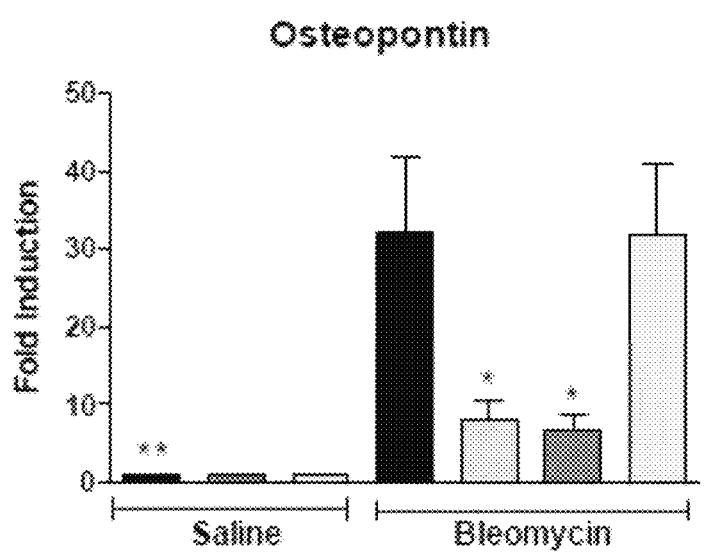

FIG. 26 shows osteopontin expression in bleomycin-exposed mice treated with vehicle, compound A and rosiglitazone.

FIG. 27 shows Fibronectin expression in bleomycin-exposed mice treated with vehicle, compound A and rosiglitazone.

Legend to FIGS. 17 to 27: in the saline group the bars represent, from left to right, vehicle, compound A (100 mg/kg) and rosiglitazone; in the bleomycin group the bars represent, from left to right, vehicle, compound A (30 mg/kg), compound A (100 mg/kg) and rosiglitazone.

Figure 28:
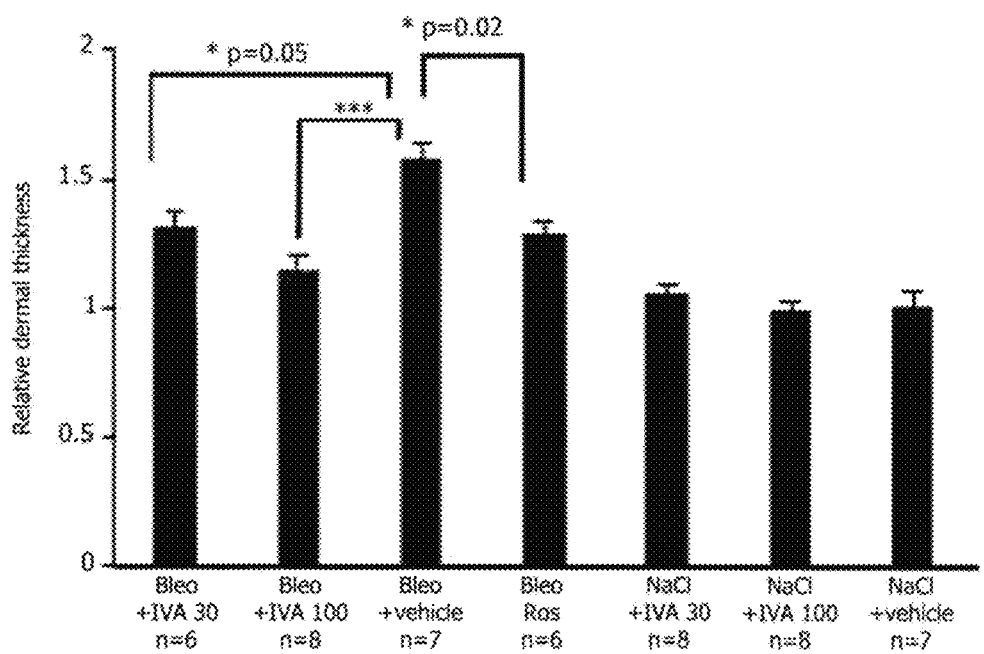

FIG. 28 shows the dermal thickness of bleomycin exposed mice treated with vehicle, compound A and rosiglitazone.

Figure 29:
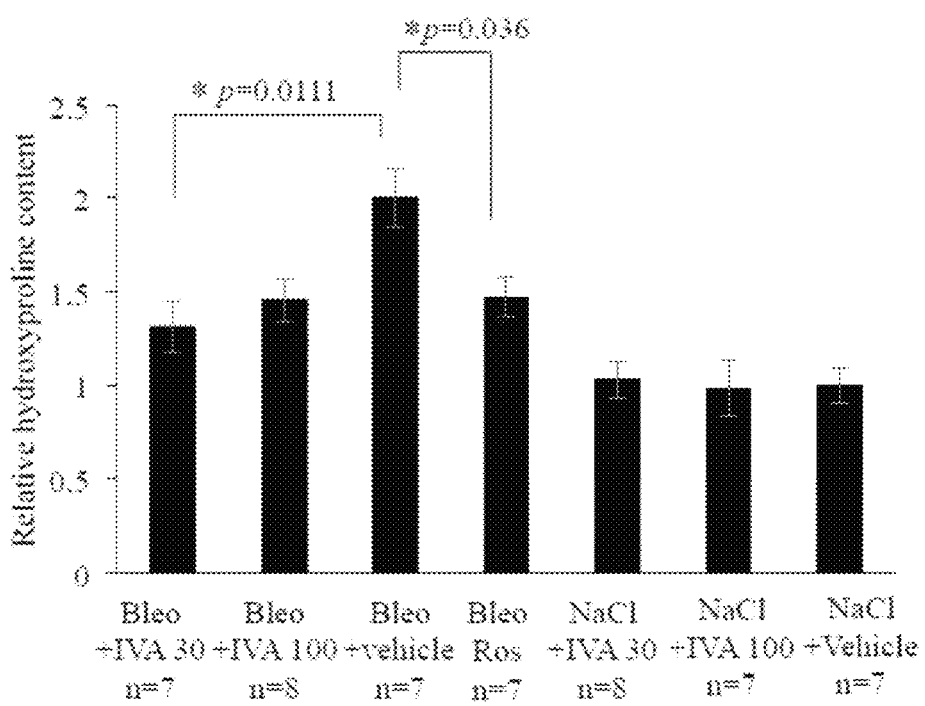

FIG. 29 shows the hydroxyproline content in bleomycin-exposed mice treated with vehicle, compound A and rosiglitazone.

Figure 30:
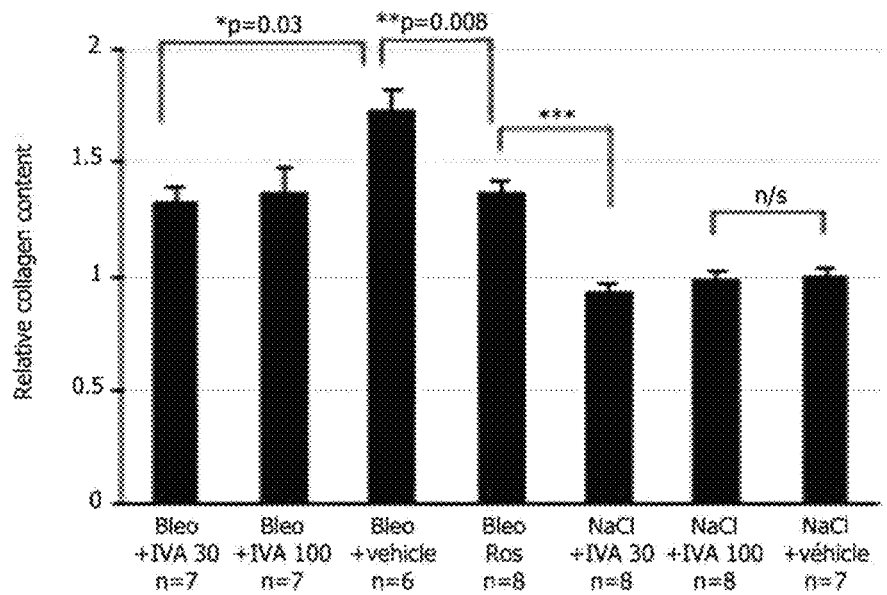

FIG. 30 shows the collagen content in bleomycin-exposed mice treated with vehicle, compound A and rosiglitazone.

Legend to FIGS. 28 to 30: Bleo=bleomycin; IVA30=compound A (30 mg/kg); IVA100=compound A (100 mg/kg); Ros=rosiglitazone.

Figure 31:
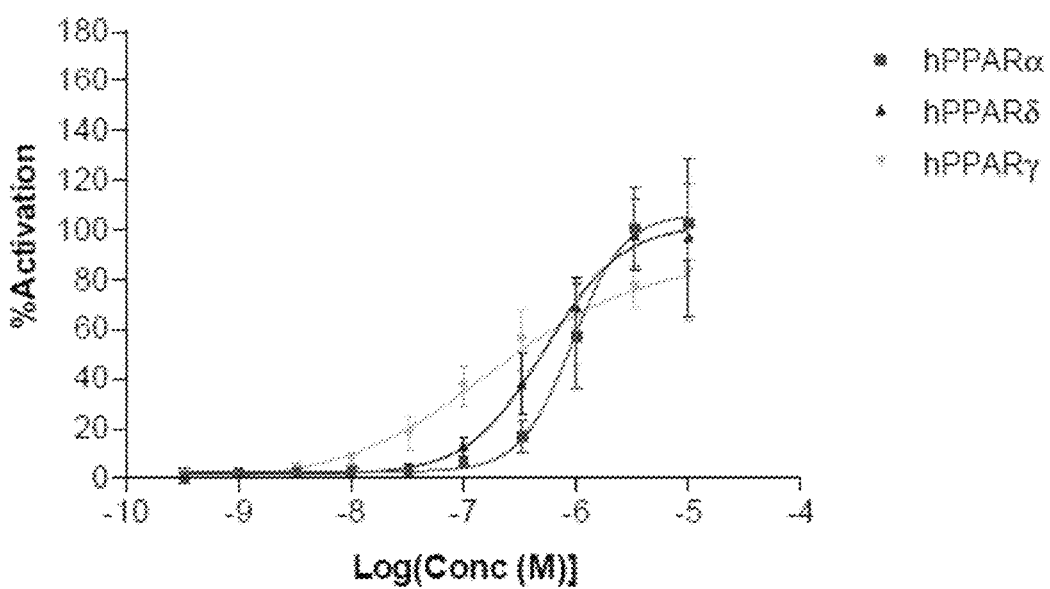

FIG. 31 shows the activation of the PPARα, γ and δ human receptors by compound A as a function of the concentration of said compound.

Figure 32:
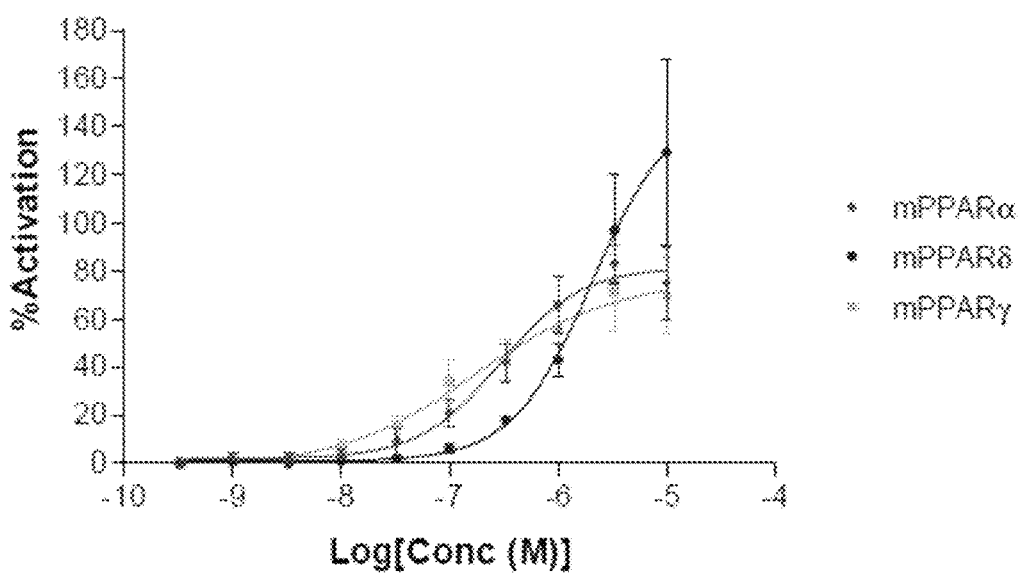

FIG. 32 shows the activation of the PPARα, γ and δ murine receptors by compound A as a function of the concentration of said compound.

Figure 33:
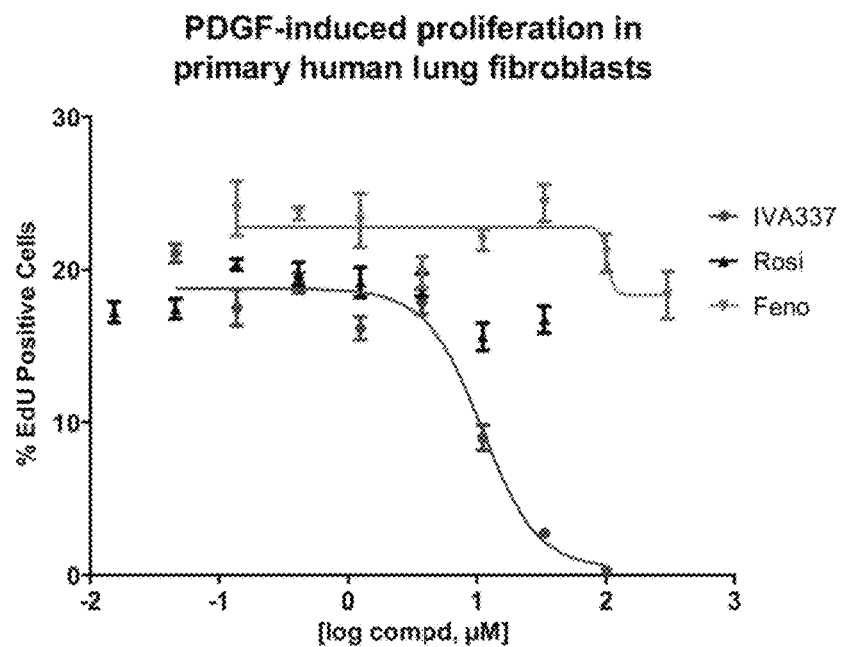

FIG. 33 shows the effect of compound A, fenofibric acid and rosiglitazone on PDGF-induced proliferation in primary human lung fibroblasts.

Figure 34:
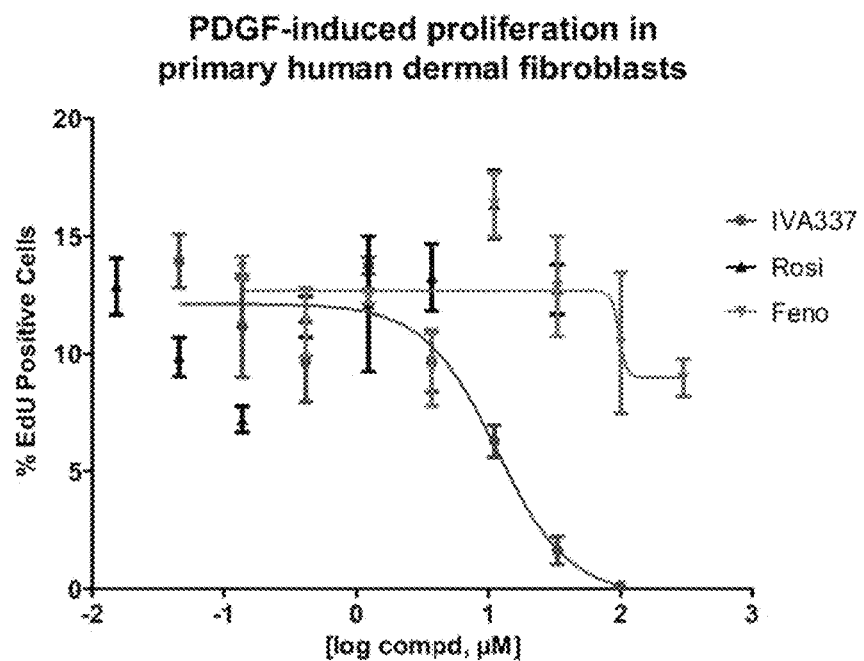

FIG. 34 shows the effect of compound A, fenofibric acid and rosiglitazone on PDGF-induced proliferation in primacy human dermal fibroblasts.

Figure 35:
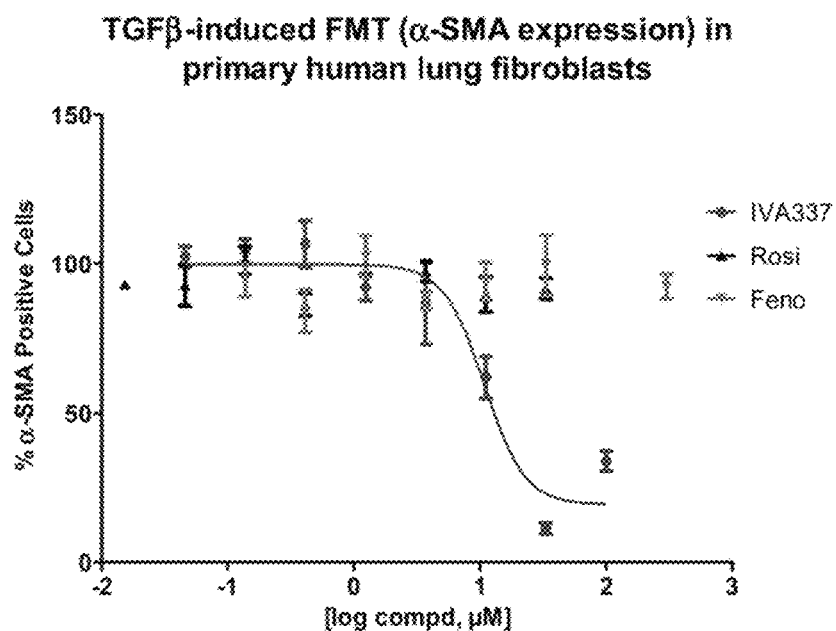

FIG. 35 shows the effect of compound A, fenofibric acid and rosiglitazone on TGFβ-induced FMT in primary human lung fibroblasts.

Figure 36:
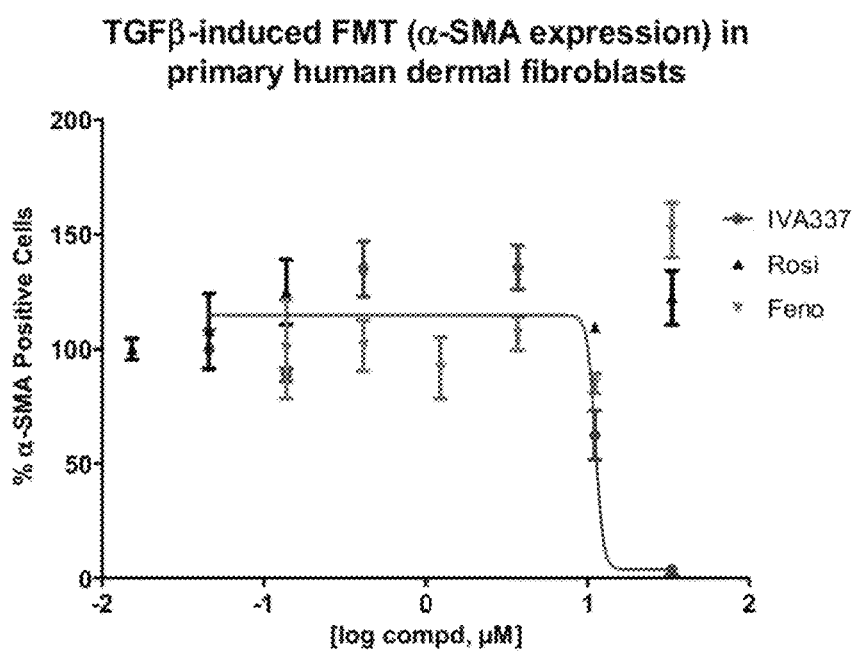

FIG. 36 shows the effect of compound A, fenofibric acid and rosiglitazone on TGFβ-induced FMT in primary human dermal fibroblasts.

Legend to FIGS. 33 to 36: Rosi=rosiglitazone; Feno=fenofibric acid.

In FIGS. 1 to 36, compound A is 5-Chloro-1-[(6-benzothiazolyl)sulfonyl]-1H-indole-2-butanoic acid.

DETAILED DESCRIPTION OF THE INVENTION

Chronic liver injury caused by fats, alcohol, virus or chemical substance may induce the activation of hepatic stellate cell for secreting a large amount of extracellular matrix such as collagen, which may lead to liver fibrosis as a consequence of the extracellular matrix over-deposition.

Chronic kidney disease (CKD) is the result of various insults so the kidney, affecting approximately 10% of the normal population. It is a progressive process marked by interstitial fibrosis. The primary aim of treatment in patients with CKD is to prevent or at least to slow progression of CKD.

Pulmonary fibrosis also called idiopathic pulmonary fibrosis (IPF), interstitial diffuse pulmonary fibrosis, inflammatory pulmonary fibrosis, or fibrosing alveolitis, is an inflammatory lung disorder and a heterogeneous group of conditions characterized by abnormal formation of fibrous tissue between alveoli caused by alveolitis comprising an inflammatory cellular infiltration into the alveolar septae with resulting fibrosis. The effects of IPF are chronic, progressive, and often fatal. A number of investigations about pulmonary fibrosis have indicated that sustained and augmented expression of some cytokines in the lung are relevant to recruitment of inflammatory cells and accumulation of extracellular matrix components followed by remodeling of the lung architecture. In particular, proinflammatory cytokines such as TNF-α and interleukin IL-1β were demonstrated to play major roles in the formation of pneumonitis and pulmonary fibrosis. In addition, profibrotic cytokines such as TGF-α and CTGF also play critical roles in the pathogenesis of pulmonary fibrosis.

Scleroderma is a disease that causes thickened skin and varying degrees of organ dysfunction resulting from small-vessel vasculopathy and immune-mediated fibrosis. The clinical manifestations of this disease are extremely heterogeneous and depend on the presence and degree of internal organ involvement. Patients can present with a spectrum of illness ranging from localized skin fibrosis only (localized scleroderma) to a systemic disorder with both cutaneous and internal organ involvement. Localized scleroderma includes various forms of cutaneous sclerosis without internal organ involvement. These forms of scleroderma can be disfiguring but only rarely require systemic therapy to control disease activity. Systemic sclerosis is further divided into two subsets of disease, depending on the degree of skin and organ involvement. The presence of diffuse systemic sclerosis denotes the presence of extensive cutaneous sclerosis over the proximal limbs, trunk, and face. Patients with limited systemic sclerosis have fibrosis limited to the hands, forearms, feet, legs and face. Both diffuse and limited systemic sclerosis are associated with internal organ involvement; however, patients with diffuse systemic sclerosis are at greater risk of clinically significant major organ dysfunction. Some patients with limited systemic sclerosis may be further classified as having the CREST syndrome, with accompanying calcinosis, Raynaud's phenomenon, esophageal dysmotility, sclerodactyly, and cutaneous telangiectasias. Scleroderma since sclerosis is a rare disorder in which patients develop vascular and fibrotic damage to internal organs in the absence of cutaneous sclerosis. The pathophysiology of systemic sclerosis involves vascular damage and activation of fibroblasts, and collagen and other extracellular proteins in various tissues are overproduced. Scleroderma is characterized by immune system activation, endothelial dysfunction, and enhanced fibroblast activity. The precise inciting events leading to the development of systemic sclerosis are currently unknown. Several cytokines including interleukin-4 and transforming growth factor-beta (TGF-β) have been implicated in fibroblast activation in patients with scleroderma. These cytokines are released from activated immune cells, fibroblasts, and endothelial cells. Activated fibroblasts elaborate structurally normal collagen and other extracellular matrix proteins in the skin and various internal organs.

The present invention is based on the finding that a pan-PPAR agonist exerts beneficial effects in the treatment of the fibrotic conditions such as those described above. In the context of the present invention, the term "pan-PPAR agonist" is intended to mean a compound which significantly activates each of the PPARα, PPARγ and PPARδ receptors, i.e. a compound which would individually be regarded as a PPARα agonist, a PPARγ agonist, and a PPARδ agonist based on its respective EC50 values. According to the present invention, significant activation of the PPARα, PPARγ and PPARδ receptors is achieved when the EC50 for each receptor is ≤$10^{-6}$ M. The EC50s for the three receptor subtypes preferably differ by less than 2 orders of magnitude (i.e. the ratio of the EC50 for two receptor subtypes is either less than 100 or greater than 0.01). In one embodiment the pan-PPAR agonist is not bezafibrate.

In one aspect, the invention therefore provides a pan-PPAR agonist for use in the treatment of a fibrotic condition.

In one embodiment, the fibrotic condition is a condition affecting any organ which can develop fibrosis, such as the heart, the lung, the liver, the kidney, the gastrointestinal tract, the skin, etc.

In a further embodiment, the fibrotic condition is selected from: liver fibrosis, fatty liver disease, non-alcoholic steatohepatitis, chronic kidney disease, a pulmonary fibrotic disorder, systemic scleroderma.

In yet a further embodiment, the fibrotic condition is a liver disease, preferably liver fibrosis, fatty liver disease, or non-alcoholic steatohepatitis.

In yet a further embodiment, the fibrotic condition is chronic kidney disease. The disease is notably selected from nephropathy (e.g. membranous nephropathy, diabetic nephropathy and hypertensive nephropathy), glomerulonephritis (e.g. membranous glomerulonephritis and membranoproliferative glomerulonephritis such as rapidly progressive glomerulonephritis), interstitial nephritis, lupus nephritis, idiopathic nephrotic syndrome (e.g. minimal change nephrotic syndrome and focal segmental glomerulosclerosis), obstructive uropathy, polycystic kidney disease (e.g. Autosomal Dominant Polycystic Kidney Disease and Autosomal Recessive Polycystic Kidney Disease), and kidney graft rejection (e.g. acute and chronic kidney rejection).

In yet a further embodiment, the fibrotic condition is a pulmonary fibrotic disorder, preferably idiopathic pulmonary fibrosis.

In yet a further embodiment, the fibrotic condition is a skin fibrosis such as systemic scleroderma.

In yet a further embodiment, which can be combined with any of the previous embodiments, the pan-PPAR agonist is intended for oral administration.

The pan-PPAR agonist can be formulated into a pharmaceutical composition for administration.

In another aspect, the invention therefore provides a pharmaceutical composition including a pan-PPAR agonist, together with a pharmaceutically acceptable excipient, for use in the treatment of a fibrotic condition as described above in the various embodiments of the first aspect of the invention. In one embodiment, the composition comprises a therapeutically effective amount of a pan-PPAR agonist. In the context of the invention, the term "therapeutically effective amount" means a sufficient amount of pan-PPAR agonist to provide the desired effect. Ultimately, the attending physician decides the appropriate amount and dosage regimen.

In yet another aspect the invention provides the use of a pan-PPAR agonist in the manufacture of a medicament for the treatment of a fibrotic condition as described above in the various embodiments of the first aspect of the invention.

In yet another aspect, the invention provides a method of treating a fibrotic condition as described above in the various embodiments of the first aspect of the invention, which comprises administering to a subject in need thereof a therapeutically effective amount of a pan-PPAR agonist. The subject is typically a mammal, preferably a human. The term "therapeutically effective amount" has the same meaning as mentioned above.

The pan-PPAR agonist will generally be administered as a formulation in association with one or more pharmaceutically acceptable excipients. The term 'excipient' is used herein to describe any ingredient other than the pan-PPAR agonist. The choice of excipient(s) will to a large extent depend on factors such as the particular mode of administration, the effect of the excipient on solubility and stability, and the nature of the dosage form.

Pharmaceutical compositions suitable for the delivery of the pan-PPAR agonist and methods for that preparation will be readily apparent to those skilled in the art. Such compositions and methods for their preparation may be found, for example, in Remington's Pharmaceutical Sciences, 19th Edition (Mack Publishing Company, 1995), incorporated herein by reference.

Oral Administration

The pan-PPAR agonist may be administered orally. Oral administration may involve swallowing, so that the compound enters the gastrointestinal tract, and/or buccal, lingual, or sublingual administration by which the compound enters the blood stream directly from the mouth. Formulations suitable for oral administration include solid, semi-solid and liquid systems such as tablets; soft or hard capsules containing multi- or nano-particulates, liquids, or powders; lozenges (including liquid-filled); chews; gels; fast dispersing dosage forms; films; ovules; sprays; and buccal/mucoadhesive patches.

Liquid formulations include suspensions, solutions, syrups and elixirs. Such formulations may be employed as fillers in soft or hard capsules (made, for example, from gelatin or hydroxypropylmethylcellulose) and typically comprise a carrier, for example, water, ethanol, polyethylene glycol, propylene glycol, methylcellulose, or a suitable oil, and one or more emulsifying agents and or suspending agents. Liquid formulations may also be prepared by the reconstitution of a solid, for example, from a sachet.

For tablet or capsule dosage forms, depending on dose, the drug may make up from 1 weight % to 80 weight % of the dosage form, more typically from 5 weight % to 60 weight % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinised starch and sodium alginate. Generally, the disintegrate will comprise from 1 weight % to 25 weight %, preferably from 5 weight % to 20 weight % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinised starch, hydroxypropyl cellulose and hydroxypropyl methylcellulose. Tablets may also contain diluents, such as lactose (monohydrate, spray-dried monohydrate, anhydrous and the like), mannitol xylitol, dextrose, sucrose, sorbitol, microcrystalline cellulose, starch and dibasic calcium phosphate dihydrate.

Tablets or capsules may also optionally comprise surface active agents, such as sodium lauryl sulfate and polysorbate 80, and glidants such as silicon dioxide and talc. When present, surface active agents may comprise from 0.2 weight % to 5 weight % of the tablet, and glidants may comprise from 0.2 weight % to 1 weight % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally comprise from 0.25 weight % to 10 weight %, preferably from 0.5 weight % to 3 weight % of the tablet.

Other possible ingredients include anti-oxidants, colorants, flavoring agents, preservatives and taste-masking agents.

Exemplary tablets contain up to about 80 weight % drug, from about 10 weight % to about 90 weight % binder, from about 0 weight % to about 85 weight % diluent, from about 2 weight % to about 10 weight % disintegrant, and from about 0.25 weight % to about 10 weight % lubricant.

Tablet blends may be compressed directly or by roller to form tablets. Tablet blends or portions of blends may alternatively be wet-, dry-, or melt-granulated, melt congealed, or extruded before tableting. The final formulation may comprise one or more layers and may be coated or uncoated; it may even be encapsulated.

Parenteral Administration

The pan-PPAR agonist may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular, intrasynovial and subcutaneous. Suitable devices for parenteral administration include needle (including microneedle) injectors, needle-free injectors and infusion techniques.

Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilisation, may readily be accomplished using standard pharmaceutical techniques well known to those skilled in the art.

The solubility of the pan-PPAR agonist used in the preparation of parenteral solutions may be increased by the use of appropriate formulation techniques, such as the incorporation of solubility-enhancing agents or technologies like SMEDDS (Self Micro Emulsifying Drug Delivery System).

Formulations for parenteral administration may be formulated to be immediate and/or modified release. Modified release formulations include delayed-, sustained-, pulsed-, controlled-, targeted and programmed release. The pan-PPAR agonist may be formulated as a suspension or as a solid, semi-solid, or thixotropic liquid for administration as an implanted depot providing modified release of the active compound. Examples of such formulations include drug-coated stents and semi-solids and suspensions comprising drug-loaded poly(dl-lactic-coglycolic)acid (PGLA) microspheres.

Inhaled/Intranasal Administration

The pan-PPAR agonist may also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler, as an aerosol spray from a pressurised container, pump, spray, atomiser (preferably an atomiser using electrohydrodynamics to produce a fine mist), or nebuliser, with or without the use of a suitable propellant, such as 1,1,1,2-tetrafluoroethane or 1,1,1,2,3,3,3-heptafluoropropane, or as nasal drops. For intranasal use, the powder may comprise a bioadhesive agent, for example, chitosan or cyclodextrin.

The pressurized container, pump, spray, atomizer, or nebuliser contains a solution or suspension of pan-PPAR agonist comprising, for example, ethanol, aqueous ethanol, or a suitable alternative agent for dispersing, solubilising, or extending release of the active, a propellant(s) as solvent and an optional surfactant, such as sorbitan trioleate, oleic acid, or an oligolactic acid.

Prior to use in a dry powder or suspension formulation, the drug product is micronized to a size suitable for delivery by inhalation (typically less than 5 microns). This may be achieved by any appropriate comminuting method, such as spiral jet milling, fluid bed jet milling, supercritical fluid processing to form nanoparticles, high pressure homogenisation, or spray drying.

Capsules (made, for example from gelatin or hydroxypropylmethylcellulose), blisters and cartridges for use in an inhaler or insufflator may be formulated to contain a powder mix of pan-PPAR agonist, a suitable powder base such as lactose or starch and a performance modifier such as l-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

A suitable solution formulation for use in an atomiser using electrohydrodynamics to produce a fine mist may contain from 1 µg to 20 mg of pan-PPAR agonist per actuation and the actuation volume may vary from 1 µl to 100 µl. A typical formulation may comprise the pan-PPAR agonist, propylene glycol, sterile water, ethanol and sodium chloride. Alternative solvents which may be used instead of propylene glycol include glycerol and polyethylene glycol.

Suitable flavours, such as menthol and levomenthol, or sweeteners, such as saccharin or saccharin sodium, may be added to those formulations of the invention intended for inhaled/intranasal administration.

Formulations for inhaled/intranasal administration may be formulated to be immediate and/or modified release using, for example, PGLA. Modified release formulations include delayed-, sustained-, pulsed-, controlled-, targeted and programmed release.

In the case of dry powder inhalers and aerosols, the dosage unit is determined by means of a valve which delivers a metered amount. Units in accordance with the invention are typically arranged to administer a metered dose or "puff" containing from 1 µg to 10 mg of pan-PPAR agonist. The overall daily dose will typically be in the range 1 µg to 200 mg which may be administered in a single dose or, more usually, as divided doses throughout the day.

Topical Administration

The pan-PPAR agonist may also be administered topically, (intra)dermally, or transdermally, to the skin or mucosa. Typical formulations for this purpose include gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated.

Other means of topical administration include delivery by electroporation, iontophoresis, phonophoresis, sonophoresis and microneedle or needle-free (e.g. Powderject™, Bioject™, etc.) injection.

Formulations for topical administration may be formulated to be immediate and/or modified release. Modified release formulations include delayed-, sustained-, pulsed-, controlled-, targeted and programmed release.

Oral and parenteral administrations are suitable irrespective of the type of fibrotic condition. Topical administration is suitable when the fibrotic condition is e.g. systemic scleroderma. Inhaled/intranasal administration is suitable when the fibrotic condition is e.g. pulmonary fibrosis or systemic scleroderma.

For oral administration, the pan-PPAR agonist can be administered to a patient at dosage levels in the range of from about 100 mg to about 3,000 mg per day, preferably, from about 500 mg to about 3,000 mg per day. The total daily dose may be administered in single or divided doses. A pharmaceutical composition according to the invention may typically contain from about 100 to about 1000 mg of pan-PPAR agonist, for example 100, 200, 500, 750 or 1000 mg of pan-PPAR agonist.

Typically suspensions of pan-PPAR agonist in 1% methylcellulose solution and in 1% methylcellulose+0.5% poloxamer were prepared. Capsules containing 25, 50 or 200 mg of pan-PPAR agonist were also prepared. IV formulations where the pan-PPAR agonist is dissolved in 30%/70% w/w PEG400/0.05 M phosphate buffer, pH 8 (25-100 µg/ml) were also prepared.

In yet a further embodiment, which can be combined with any of the previous embodiments or any of the aspects of the invention, the pan-PPAR agonist is 5-Chloro-1-[(6-benzothiazolyl)sulfonyl]-1H-indole-2-butanoic acid (also referred to as "compound A"). Compound A and its method of preparation are described in WO 2007/026097. It has been found that compound A activates each of the PPARα, PPARγ and PPARδ receptors. Compound A can be used in the context of the present invention in the form of one of its pharmaceutically acceptable salts or solvates. The term 'solvate' is used herein to describe a molecular complex comprising compound A and one or more pharmaceutically acceptable solvent molecules, for example, ethanol. The term 'hydrate' is employed when said solvent is water. Pharmaceutically acceptable salts of compound A include the acid addition and base salts thereof.

Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts.

Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts. Hemisalts of acids and bases may also be formed, for example, hemisulphate and hemicalcium salts.

Pharmaceutically acceptable salts of compound A may be prepared by one or more of three methods:

(i) by reacting the compound with the desired acid or base;

(ii) by removing an acid- or base-labile protecting group from a suitable precursor of the compound or by ring-opening a suitable cyclic precursor, for example, a lactone or lactam, using the desired acid or base; or (iii) by converting one salt of the compound to another by reaction with an appropriate acid or base or by means of a suitable ion exchange column.

All three reactions are typically carried out in solution. The resulting salt may precipitate out and be collected by filtration or may be recovered by evaporation of the solvent. The degree of ionisation in the resulting salt may vary from completely ionised to almost non-ionised.

The invention is illustrated by the following examples.

Example 1: Effect of Compound A on the Development of Carbon Tetrachloride-Induced Liver Fibrosis in Mice, and Comparison with Known PPARγ Agonist It has been reported (Yao T et al., Am J Physiol. 1994 September; 267(3 Pt 1):G476-84) that carbon tetrachloride ($CCl_4$) induces hepatocyte mitochondrial dysfunction and oxidative stress in a mouse model, leading to collagen deposition and liver fibrosis. The effect of compound A and rosiglitazone, a known PPARγ agonist, has accordingly been assessed in a murine model of $CCl_4$-induced liver fibrosis.

Mice were daily orally treated tor 22 days with compound A at two different doses (30 and 100 mg/kg/day) and with the PPARγ reference compound rosiglitazone at 5 mg/kg/day. At the end of the treatment, animals were sacrificed and plasma samples and livers were harvested. Collagen deposition and expression of genes that are known to be involved in liver inflammation and fibrosis were quantified and some related plasmatic biomarkers were measured.

$CCl_4$-exposed mice orally treated with vehicle for days displayed a hepatic fibrosis as shown by the statistically significant increase in collagen level in liver tissue. Treatment with compound A significantly reduced hepatic fibrosis by 80% (30 mg/kg/day) and 89% (100 mg kg day), respectively and improved many of the related markers. Treatment with rosiglitazone reduced hepatic fibrosis by 54% only while most markers were either unchanged or even worsened.

MATERIALS AND METHODS

The experiments were carried out using 56 male C57BL/6J mice (JANVIER LABS, C.S. 4105, Saint-Berthevin, France), weighing 21-24 g at the beginning of the experiment. The animals were housed in groups of 3-10 in polypropylene cages (floor area=1032 $cm^2$) under standard conditions: room temperature (22±2° C.), hygrometry (55±10%), light/dark cycle (12 h/12 h), air replacement (15-20 volumes/hour), water and food (SDS, RM1) ad libitum. Mice were allowed to habituate for at least 5 days prior to experimentation. Mice were numbered by marking their tail using indelible markers.

Ready-to-use suspensions of compound A (3 mg ml and 10 mg/mL) and rosiglitazone (0.5 mg/mL) were stored at 5±3° C. Ready-to-use formulations of vehicle (methyl cellulose 400 cP 1%+0.1% Poloxamer 188) were also stored at 5±3° C. Carbone tetrachloride ($CCl_4$) (Sigma Chemical co, Saint Quentin Fallavier, France) was freshly prepared each day of dosing in sunflower oil (v/v, 1/11).

Dosing

Mice were allocated to the following groups:
1. Sunflower oil (twice a week for 3 weeks, ip)/vehicle (once a day for 22 days po), n=7,
2. Sunflower oil (twice a week for 3 weeks, ip)/compound A (100 mg/kg/d once a day for 22 days po), n=8,
3. Sunflower oil (twice a week for 3 weeks, ip)/rosiglitazone (5 mg/kg/d once a day for 22 days po), n=8
4. $CCl_4$ (3.5 mL/kg, twice a week for 3 weeks, ip)/vehicle (once a day for 22 days po), n=8
5. $CCl_4$ (3.5 mL/kg, twice a week for 3 weeks, ip)/compound A (30 mg/kg/d once a day for 22 days po), n=8,
6. $CCl_4$ (3.5 mL/kg, twice a week for 3 weeks, ip)/compound A (100 mg/kg/d once a day for 22 days po), n=7
7. $CCl_4$ (3.5 mL/kg, twice a week for 3 weeks, ip)/rosiglitazone (5 mg/kg/d once a day for 22 days po), n=8.

Two days a week for 3 weeks, mice were intraperitoneally administered in the morning with either 100 μL of $CCl_4$ (3.5 mL kg in sunflower oil (v/v, 1/11)) or 100 μL of sunflower oil. In parallel, mice were orally treated once a day for 22 days (day 0 to day 21) with vehicle, compound A or rosiglitazone. On days with concomitant administrations of vehicle, compound A or rosiglitazone and $CCl_4$, vehicle, compound A or rosiglitazone was administered 6 hours before sunflower oil or $CCl_4$ administration. The volume of administration of test compounds was 10 mL/kg body weight for oral administrations.

Terminal Blood Sampling

On day 21, 2 hours after dosing, animals were anaesthetised with pentobarbital (60 mg/kg, ip) and blood was collected using cardiac puncture. The exact time of dosing and time of sample collection were noted for each animal. Blood sampling (0.9 ml, of total blood) was placed in pre-chilled 2-mL lithium-heparin collection tubes. The blood samples were gently mixed, placed on crushed ice and centrifuged within 30 min of sampling at approximately 1500×g for 10 min at approximately +4° C. For each blood sampling, the resultant plasma was separated into 2 aliquots (at least 100 μL each) and transferred using disposable plastic material into polypropylene tubes. The samples were immediately transferred in the upright position to a freezer where they were kept at 20° C.

After terminal blood sampling, liver tissue was removed:
A first tissue sample (about 50 mg) was harvested and fixed with paraformaldehyde, and at 5±3° C.,
A second tissue sample (200 mg) was frozen in liquid nitrogen and kept at −20° C.

Measured Parameters

Collagen

For the quantification of collagen, sections were stained with Picro-Sirius red and counterstained with Mayer's haemoatoxylin. All slides were digitized and 5 non overlapping fields of 3 different sections were randomly analysed by means of the image J software (version 1.42, N.I.H., USA). For all slides, analysis was performed by a single experimenter strictly in the same conditions.

Gene Expression mRNA extraction was performed on small frozen liver samples (50-100 mg). Briefly, samples were cryogenically ground with mortar and pestle. Samples were subsequently homogenized using marble (2×5 mn) and 1 ml of Qiazol lysis reagent (Qiagen Ref 79306) in a Retsch MM300 apparatus. RNA extraction on liver homogenates was finalized with Qiagen Rneasy lipid Kit (Ref 74804) according to the manufacturer's instructions. RNA quantify was determined with Nanodrop (ND2000 Thermo Scientific) and RNA quality was verified with Bioanalyzer (2100 Agilent Technology).

Random-primed cDNA synthesis was carried out on 100 ng total RNA using the Iscript kit (BIORAD ref 170-8891) according to the manufacturer's instructions Real-time PCR was carried out with 7.5 ng RNA equivalents on an ABI Prism 7900 Sequence Detection System (APPLIED BIOSYSTEMS) using Iq ITaq SYBR Green Universal Rox (Ref 1725124 Biorad) and using dedicated QPCR primers. For some mRNA transcripts, quantification was performed using TaqMan probes labeled with the fluorochrome FAM and using Universal PCR MasterMix No AmpErase UNG (APPLIED BIOSYSTEMS ref 4324020). The primers used for the assays are listed in the following table:

| Target Name | Full target name | Primer names | Sequences (5'-3') |
|---|---|---|---|
| Rplp0 | ribosomal protein, large, P0 | Fw2Rplp0 PE<br>Rev2Rplp0 PE | ctgatgggcaagaacaccat (SEQ ID NO: 1)<br>gtgaggatcctccttggtgaa (SEQ ID NO: 2) |
| Tgfb1 | transforming growth factor, beta 1 | MTgfb1FW<br>MTgfb1REV | accggccttcctgctcctc (SEQ ID NO: 3)<br>gccgcacacagcagttcttc (SEQ ID NO: 4) |
| Col1a1 | collagen, type 1, alpha 1 | MCol1a1FW<br>MCol1a1REV | aaaggtgctgatggttctcc (SEQ ID NO: 5)<br>gggaccgggaggaccactgg (SEQ ID NO: 6) |
| Fn1 | fibronectin 1 | MFn1FW<br>MFn1REV | gttgtctgacgctggctttaag (SEQ ID NO: 7)<br>cccacttctctccgatcttgta (SEQ ID NO: 8) |
| Acta 2 (α-SMA) | Actin, alpha 2, smooth muscle, aorta | Macta2FW<br>Macta2REV | cagggagtaatggttggaatg (SEQ ID NO: 9)<br>tttccatgtcgtcccagttg (SEQ ID NO: 10) |
| Ccl2 (MCP-1) | Chemokine (C C motif) ligand 2 | MCcl2FW<br>MCcl2REV | aggtccctgtcatgcttctg (SEQ ID NO: 11)<br>gcctactcattgggatcatc (SEQ ID NO: 12) |

Real Time PCR was performed on ABI PRISM 7900 apparatus Raw data from ABI7900 were exported in text format. Analysis was performed on Excel, the relative quantity of transcript were calculated using the "Delta Delta CT method" (Livak et al. Methods 2001), using Rp1p0 as housekeeping gene tor normalization and mean data from the non-treated animals (vehicle group) as reference control. Each RNA samples were reverse transcribed and quantified in triplicate.

Liver Biomarkers

Protocol of Liver Proteins Extraction:

Extraction with T-PER®: Tissue Protein Extraction Reagent, prod#78510 (lot: NG174004), Thermo Scientific with: Halt Protease Inhibitor Single-Use Cocktail, EDTA-free (100×)—Prod#78425—Lot #NL178051 Thermo Fischer.

Samples of liver and supernatants were kept on ice during all experiment. For extraction, the manufacturer recommends 10 mg of tissue for 100 μl T-Per+1 μl "Halt-protease" (100×).

50 ml of T-Per buffer were prepared to which 500 μl of "Halt-protease" (100×) were added, and the mixture was kept on ice. Samples of 50 to 70 mg of liver just thawed were weighed and cut into small pieces, and 1 ml of cold PBS was added to wash the tissue. The mixture was centrifuged at 500 g during 5 min at 4° C., and the supernatant was discarded. 100 μl/10 mg of T-Per+antiproteases (100×) were added, crushing the liver with a Potter, with 5 or 6 twists, up and down. The mixture was centrifuged at 10000 g during 5 min at 4° C. The supernatant was removed, aliquoted and kept at −20° C. for the subsequent measurement of biomarkers. Samples of 10 μl were used to dose proteins by the BCA technique, after dilution $1/10^{ème}$ in $H_2O$ mq following the procedure described in MOS: BAP-05-062-01 (Kit BCA—Pierce BCA protein assay kit—Pierce Thermo scientific, Ref: 23225).

All proteins were quantified with ELISA Kit, according to the instructions of the manufacturers:

TIMP-1: Mouse TIMP-1, R&D SYSTEMS®, Ref: TM100

TGF-β1: Quantikine Mouse/Rat/Porcine Canine TGF-β1 immunoassay, R&D SYSTEMS®, ref: MB100B Data Processing and Statistical Analysis All parameters were analysed using Graph pad software (version 5.1). The parameters were analysed as followed:

Using student's t test for independent samples to compare group 1 versus group 4 to validate the experiment (effect of $CCl_4$).

Using student's t test for independent samples to compare group t versus group 2 and group 1 versus group 3 to investigate the effect of compound A or rosiglitazone alone, Using one-way ANOVA (treatment) to compare group 4 versus compound A treated groups (5, 6) to investigate the effect of compound A on $CCl_4$-induced liver fibrosis. As ANOVA was found significant, a Dunnett's test was used, Using student's t test for independent samples to compare group 4 versus rosiglitazone treated-group (group 7) to investigate the effect of rosiglitazone on $CCl_4$-induced liver fibrosis.

In FIGS. 1 to 7, * denotes a p-value<0.05;  denotes a p-value<0.01; * denotes a p-value<0.001.

RESULTS

1/Plasma Triglycerides

Figure 1:
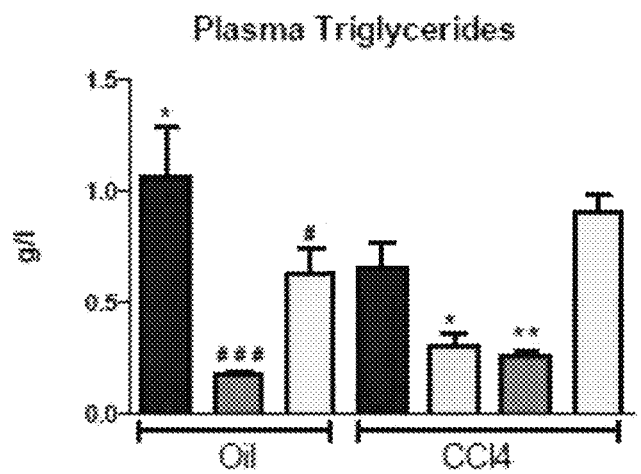
FIG. 1 shows plasma, triglycerides levels of $CCl_4$-exposed mice treated with vehicle, compound A and rosiglitazone.

In $CCl_4$-exposed mice, compound A (30 and 100 mg/kg/day) significantly reduced plasma triglycerides compared to vehicle (p<0.05 and p<0.01, respectively) whereas rosiglitazone increased plasma triglycerides without teaching significance (FIG. 1).

2/Collagen Deposition

Figure 2:
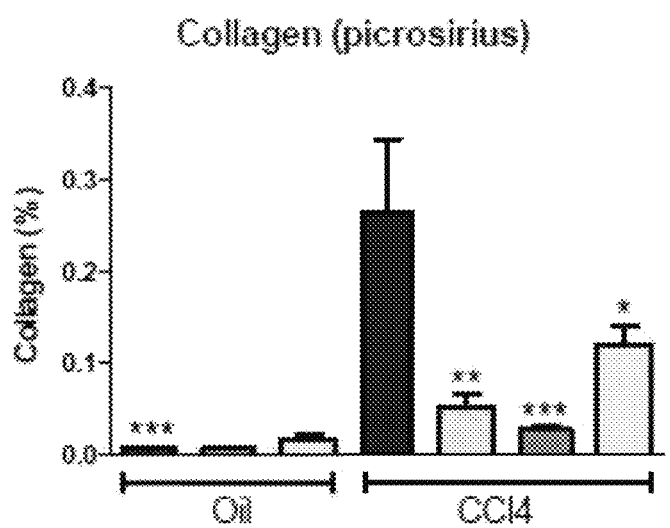
FIG. 2 shows collagen deposition in $CCl_4$-exposed mice treated with vehicle, compound A and rosiglitazone.

In $CCl_4$-exposed mice compound A (30 and 100 mg/kg/day) significantly decreased collagen levels compared to vehicle (~80%, p<0.01 and p<0.001, respectively), and rosiglitazone significantly decreased collagen levels (−54%, p<0 (FIG. 2).

3/TGFβ-1 Expression

Figure 3:
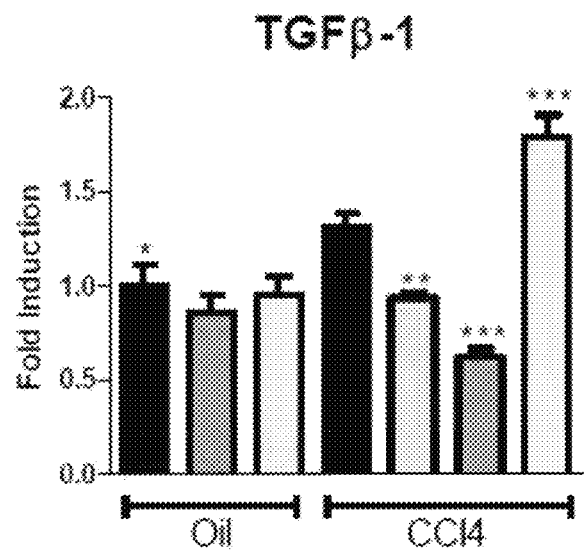
FIG. 3 shows TGFβ-1 expression in $CCl_4$-exposed mice treated with vehicle, compound A and rosiglitazone.

In $CCl_4$-exposed mice, compound A (30 and 100 mg/kg/day) significantly inhibited the expression of TGFβ-1 compared to vehicle (p<0.01 and p<0.001, respectively) whereas rosiglitazone significantly upregulated the expression of TGFβ-1 (p<0.001) (FIG. 3).

4/Collagen Type I, Alpha I (Col1a) Expression

Figure 4:
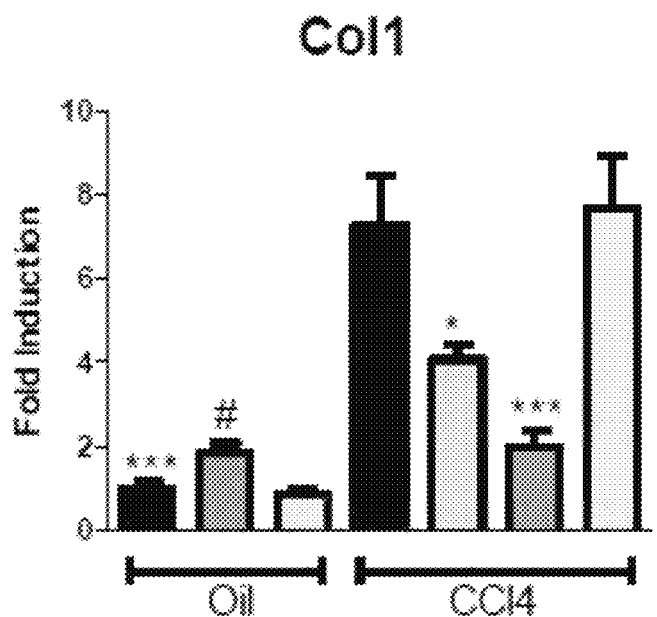
FIG. 4 shows Col1a expression in $CCl_4$-exposed mice treated with vehicle, compound A and rosiglitazone.

In $CCl_4$-exposed mice, compound (30 and 100 mg/kg/day) significantly inhibited the expression of Col1a compared to vehicle (p<0.05 and p<0.001, respectively) whereas rosiglitazone upregulated the expression of Col1a without reaching significance (FIG. 4).

5/α-SMA Expression

Figure 5:
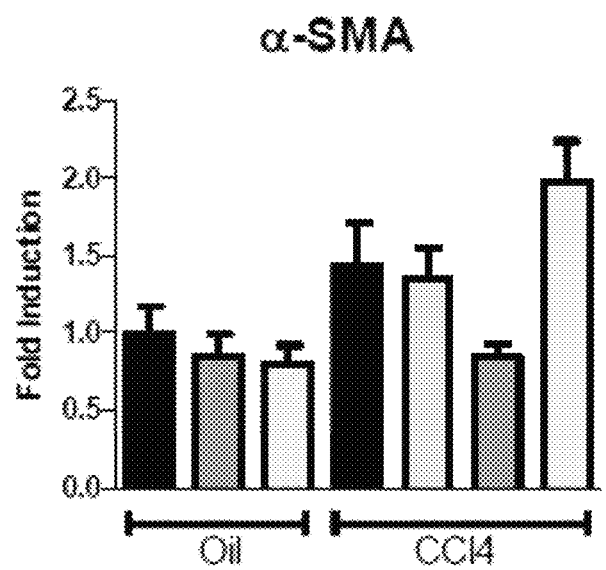
FIG. 5 shows α-SMA expression in $CCl_4$-exposed mice treated with vehicle, compound A and rosiglitazone.

In CCl$_4$-exposed mice, compound A (100 mg/kg/day) inhibited the expression of α-SMA compared to vehicle without reaching significance whereas rosiglitazone upregulated the expression of α-SMA without reaching significance (FIG. 5).

6/MCP-1 Expression

Figure 6:
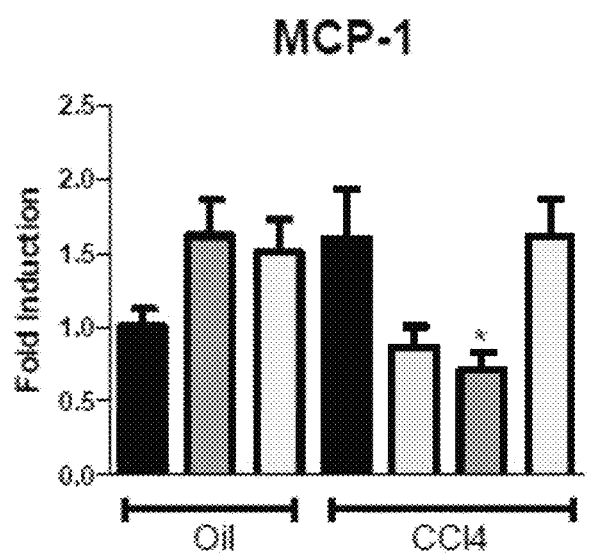
FIG. 6 shows MCP-1 expression in $CCl_4$-exposed mice treated with vehicle, compound A and rosiglitazone.

In CCl$_4$-exposed mice, compound A (100 mg/kg/day) significantly inhibited the expression of MCP-1 compared to vehicle (p<0.05) whereas rosiglitazone had no effect (FIG. 6).

7/Fibronectin Expression

In CCl$_4$-exposed mice, compound A (30 and 100 mg/kg/day) significantly inhibited the expression of fibronectin compared to vehicle (p<0.001) whereas rosiglitazone upregulated the expression of fibronectin without reaching significance (FIG. 7).

The above results show that oral administration of compound A (30 or 100 mg/kg/day) for 22 days in the male C57BL/6J mouse reduced CCl$_4$-induced liver fibrosis. A dose-dependent effect was obtained with compound and a maximal 90% decrease in collagen levels was observed with compound A at 100 mg/kg/day and improved significantly most of the associated markers. In contrast, rosiglitazone had a much less marked effect while at most having no effect on other markers.

Example 2: Effect of Compound A on the Development of Anti-GBM Induced Glomerulonephritis in Mice, and Comparison with Known PPARγ Agonists and with a Known ICE Anti-GBM (Glomerular Basement Membrane) induced glomerulonephritis in mice is a commonly used in vivo model to evaluate the potential of new chemical entities against CKD). The effect of compound A of rosiglitazone and pioglitazone (known PPARγ agonists), and of captopril (a known ICE—inhibitor of the (angiotensin) conversion enzyme), has accordingly been assessed in such a model.

Mice were daily orally treated for 7 days with compound A at two different doses (and 100 mg/kg/day), with the PPARγ reference compounds rosiglitazone (at 3 mg/kg/day) and pioglitazone (at mg/kg/day), and with the reference ICE compound captopril at 10 mg/kg/day. At the end of the treatment, animals were sacrificed and plasma samples and kidneys were harvested. Expression of genes that are known to be implicated in CKD was quantified and plasmatic levels of kidney parameters were measured.

Anti-GBM exposed mice orally treated with vehicle for 7 days displayed a glomerulonephritis and a fibrosis as shown by the statistically significant increase of urinary urea, albuminuria, kidney osteopontin, kidney MCP-1 protein levels Col1 and Col3 expression compared to vehicle. Treatment with compound A in 30 and 100 mg/kg/day for 7 days reduced urinary urea, albuminuria, kidney osteopontin, kidney MCP-1 levels, Col1 and Col3 mRNA expression computed to vehicle (with significance at 100 mg/kg/day). In comparison, captopril had an effect similar to that of compound A on urinary urea, albuminuria, kidney osteopontin, kidney MCP-1 protein levels but did not significantly reduce Col1 and Col3 expression; rosiglitazone and pioglitazone, however, significantly increased kidney osteopontin and kidney MCP-1 levels compared to vehicle.

MATERIALS AND METHODS

The experiments were carried out using female C5BL/6J mice (CERJ Janvier, route des Chênes secs, Le Genest Saint Isle—France), aged 8-10 weeks at the beginning of the experiment. The animals were randomly assigned to polypropylene boxes (floor area=1032 cm$^2$) by groups of 3-4, based on weight. Mice were individually marked on the ear. They were allowed to habituate for a week prior to experimentation under standard conditions: room temperature (22±2° C.), hygrometry (55±10%), light/dark cycle (12 h/12 h), air replacement (15-20 volumes/hour), water and food (SDS, RM1) ad libitum.

Ready-to-use suspensions of compound A (3 mg/mL and 10 mg/mL, corresponding to a dose of 30 mg/kg and 100 mg/kg, respectively) in vehicle [1% Methylcellulose (METOLOSE SM400, 400 Cps)+0.1% Poloxamer 188] were stored at 5° C. until use.

Ready-to-use suspensions of rosiglitazone (0.3 mg/mL, corresponding to a dose of 3 mg/kg) in vehicle were stored at 5° C. until use.

Ready-to-use suspensions of pioglitazone (3 mg/mL, corresponding to a dose of 30 mg/kg) in vehicle were stored at 5° C. until use.

Ready-to-use suspensions of captopril (1 mg/mL, corresponding to a dose of 10 mg/kg) in vehicle were stored at 5° C. until use.

Sheep IgG antibody (ab37385, Abcam) preparation was carried out at 4° C. on ice. The antibody was dissolved in physiological serum so as to obtain a 4 mg/ml solution. Separately, complete Freund's adjuvant (CFA) was homogenized with a vortex. A 5 ml luer lock syringe was filled with 2.5 ml of CFA. Another 5 ml luer lock syringe was filled with 2.5 ml of Sheep IgG solution. Both syringes were connected with a micro emulsion needle taking care to remove all air bubbles. Sheep IgG solution was passed in CFA. The mixture between the two syringes was repeatedly forced during 5 minutes until a noticeable increase of resistance was observed. The micro emulsion needle was then replaced by an inox coupler luer female/luer female. The mixture between the two syringes was again forced during a few minutes. The surface tension in water was then tested. 1 ml luer lock syringes were filled, taking care to remove air bubbles. A 23G needle was added that the syringes were stored at 4° C. until use.

Sheep Anti-Rat Glomeruli (GBM) Serum ((PTX-001S, Probetex) was stored at 5° C. until use.

Dosing

Mice were allocated to the following groups:

| Group | Mice number | Immunization Emulsion Sheep IgG/HR37Ra | Challenge anti-GBM antibody | Treatment |
|---|---|---|---|---|
| 1 | 10 | 200 μg/500 μg | no | Vehicle |
| 2 | 10 | | 300 μl | Vehicle |
| 3 | 10 | | | Captopril 10 mg/kg |
| 4 | 10 | | | Rosiglitazone 3 mg/kg |
| 5 | 10 | | | Pioglitazone 30 mg/kg |
| 6 | 10 | | | Compound A 30 mg/kg |
| 7 | 10 | | | Compound A 100 mg/kg |

5 days before anti-GBM antibody administration, animals were immunized by subcutaneous injection on three sites (one over each hip and one in the scruff of the neck) of 100 µl of Sheep IgG/CFA emulsion (200 µg of Sheep IgG/100 µg of *Mycobacterium tuberculosis* H37Ra), under $O_2$/isoflurane (1 L/3%) anesthesia.

On day 0, mice were weighed and placed under a heat lamp ramp for about 20-30 minutes to allow vasodilatation of caudal veins and better visibility tor injection. Each animal was restrained in an injection cone. Mice were given an intravenous injection of 300 µl of anti-GBM antibody serum. Mice were then orally administered with compound A, rosiglitazone, pioglitazone and captopril, and treatment was continued once a day (in the morning) for a further 7 days. Mice were weighed approximately every other day.

On day 6 mice were weighed and transferred into a diuresis box where they stayed for 24 h. Bibs were weighed before and after diuresis in order to measure the amount of water taken. On day 7 mice were weighed, received oral treatment and were returned in their initial box. Urines were collected, centrifuged, measured and several aliquots were frozen at −80'T for subsequent assays (urea, creatinine, albumin . . . ).

In the afternoon of day 7 mice were anesthetized with a mixture $O_2$/isoflurane 1 L/3%) and blood sampling was performed, in the retroorbitary sinus, with a Pasteur pipette. 400 µl of whole blood were transferred in a dry microtube. Sera were obtained after 30 min of clotting and 2 centrifugations at 6000 rpm for 15 minutes, at 4° c. Sera were aliquoted and frozen at −80° C. for subsequent assays (urea, creatinine, proteins, adiponectin). Then, mice were euthanized by cervical dislocation, and kidneys were harvested and weighed. The cortex of one kidney per mouse was isolated. Small pieces were kept for subsequent RNA expression analysis as detailed below. The rest was directly frozen in liquid nitrogen for subsequent assays (TGFbeta-1, OPN, MCP1 . . . ). Of the remaining kidney, one half was placed in an individual histological cassette in 10% buffered formalin for 24 hours for histological analysis.

Measured Parameters

Gene Expression mRNA extraction was performed on small frozen kidney samples (50-100 mg). Briefly, samples were cryogenically ground with mortar and pestle. Samples were subsequently homogenized using marble (2×5 mn) and 1 ml of Qiazol lysis reagent (Qiagen Ref 79306) in a Retsch MM300 apparatus. RNA extraction on kidney homogenates was finalized with Qiagen Rneasy lipid Kit (Ref 74804) according to the manufacturer's instructions. RNA quantity was determined with Nanodrop (ND2000 Thermo Scientific) and RNA quality was verified with Bioanalyzer (2100 Agilent Technology).

Random-primed cDNA synthesis was carried out on 100 ng total RNA using the Iscript kit (BIORAD ref 170-8891) according to the manufacturer's instructions. Real-time PCR was carried out with 7.5 ng RNA equivalents on an ABI Prism 7000 Sequence Detection System (APPLIED BIOSYSTEMS) using Iq ITaq SYBR Green Universal Rox (Ref 1725124 Biorad) and using dedicated QPCR primers. For some mRNA transcripts, quantification was performed using TaqMan probes labeled with the fluorochrome FAM and using Universal PCR MasterMix No AmpErase UNG (APPLIED BIOSYSTEMS ref 4324020). The primers used for the assays are listed in the following table:

| Target Name | Full target name | Primer names | Sequences (5'-3') |
|---|---|---|---|
| Rplp0 | ribosomal protein, large, P0 | Fw2Rplp0 PE<br>Rev2Rplp0 PE | ctgatgggcaagaacaccat (SEQ ID NO: 1)<br>gtgaggtcctccttggtgaa (SEQ ID NO: 2) |
| Tgfbr1 | transforming growth factor, beta receptor 1 | MTgfbr1FW<br>MTgfbr1REV | ggtcttgcccatcttcacat (SEQ ID NO: 13)<br>caacaggttccatttttcttca (SEQ ID NO: 14) |
| Col1a1 | collagen, type 1, alpha 1 | MCol1a1FW<br>MCol1a1REV | aaaggtgctgatggttctcc (SEQ ID NO: 5)<br>gggaccgggaggaccactgg (SEQ ID NO: 6) |
| Col3a1 | collagen, type III, alpha 1 | MCol3a1FW<br>MCol3a1REV | gggatcaaatgaaggcgaat (SEQ ID NO: 15)<br>tgggtagtctcattgccttgc (SEQ ID NO: 16) |

Real Time PCR was performed on ABI PRISM 7900 apparatus Raw data from ABI7900 were exported in text format. Analysis was performed on Excel, the relative quantity of transcript were calculated using the "Delta Delta CT method" (Livak et al. Methods 2001), using Rplp0 as housekeeping gene for normalization and mean data from the non-treated animals (vehicle group) as reference control. Each RNA samples were reverse transcribed and quantified in triplicate.

Urine, Plasma and Kidney Biomarkers

Serum and urinary assays (urea, creatinine, albumin, and proteins) were carried out with a Konelab apparatus and corresponding colorimetric tests.

Micro-albuminuria was assayed with a fluorescent kit: Albumin Blue Fluorescent Assay (Active Motif, Ref: 15002).

All kidney proteins were quantified with ELISA Kit, according to the instructions of the manufacturers:

Osteopontin: Quantikine Mouse Osteopontin immunoassay, R&D SYSTEMS®, Ref: MOST00

MCP-1: Quantikine Mouse CCL2/JE/MCP-1 ELISA Kit, R&D SYSTEMS®, ref: MJE00

Data Processing and Statistical Analysis

All parameters were analysed using Graphpad software (version 5.1). The parameters were analysed using one-way ANOVA (treatment) to compare groups (1, 2, 3, 4, 5, 6 and 7). When ANOVA was found significant, a Dunnett's test was used to compare group 2 to all other groups.

In FIGS. 8 to 16, * denotes a p-value<0.05;  denotes a p-value<0.01; * denotes a p-value<0.001.

RESULTS

1/Serum Urea

In anti-GBM-exposed mice, compound A (100 mg/kg/day) significantly reduced urea levels compared, to vehicle (p<0.01) whereas captopril reduced urea level without reaching significance and both rosiglitazone and pioglitazone increased urea levels without reaching significance (FIG. 8).

2/Urinary Volume

In anti-GBM-exposed mice, compound A (30 and 100 mg/kg/day) reduced urinary volume compared to vehicle without reaching significance, whereas captopril also reduced urinary volume without reaching significance, and rosiglitazone and pioglitazone each increased urinary albumin without reaching significance (FIG. 9).

3/Urinary Albumin

In anti-GBM-exposed mice, compound A (100 mg/kg/day) reduced albumin levels compared to vehicle without reaching significance, whereas captopril also reduced albumin levels without reaching significance, rosiglitazone increased albumin levels without reaching significance, and pioglitazone significantly increased albumin levels ($p<0.001$) (FIG. 10).

4/Kidney Osteopontin

In anti-GBM-exposed mice, compound A (100 mg/kg/day) significantly reduced osteopontin levels compared to vehicle ($p<0.05$), whereas captopril also significantly reduced osteopontin levels ($p<0.05$), and rosiglitazone and pioglitazone each significantly increased osteopontin levels ($p<0.01$ and $p<0.05$, respectively) (FIG. 11).

5/Kidney MCP-1

In anti-GBM-exposed mice, compound A (100 mg/kg/day) significantly reduced MCP-1 levels compared to vehicle ($p<0.001$), whereas captopril also significantly reduced MCP-1 levels ($p<0.01$), and rosiglitazone and pioglitazone each significantly increased MCP-1 levels ($p<0.05$) (FIG. 12).

6/TGFβR-1 Expression

In anti-GBM-exposed mice, compound A (100 mg/kg/day) significantly inhibited TGFβR-1 expression compared to vehicle ($p<0.01$), whereas captopril had no effect on TGFβ-R1 expression, and rosiglitazone and pioglitazone each upregulated TGFβR-1 expression without reaching significance, (FIG. 13).

7/Collagen Type I, Alpha I (Col1a) Expression

In anti-GBM-exposed mice, compound A (100 mg/kg/day) significantly inhibited Col1a expression compared to vehicle ($p<0.01$), whereas captopril had no effect on Col1a expression, and rosiglitazone and pioglitazone each significantly upregulated Col1a expression ($p<0.001$) (FIG. 14).

8/Collagen Type III, Alpha I (Col3a) Expression

In anti-GBM-exposed mice, compound A (100 mg/kg/day) significantly inhibited Col3a expression compared to vehicle ($p<0.001$), whereas captopril had no effect on Col3a expression, rosiglitazone significantly upregulated Col3a expression ($p<0.05$), and pioglitazone upregulated Col3a expression without reaching significance (FIG. 15).

9/Pathological Glomeruli

In anti-GBM-exposed mice, compound A (100 mg/kg/day) significantly reduced the number of pathological glomeruli ($p<0.001$) (FIG. 16).

Example 3: Effect of Compound A on the Development of Bleomycin-Induced Pulmonary Fibrosis in Mice, and Comparison with a Known PPARγ Agonist Bleomycin-induced pulmonary fibrosis in mice is an in vivo model commonly used to evaluate the anti-fibrotic potential of new chemical entities (Corbel et al, 2001; Manoury et al, 2006). The effect of compound A and rosiglitazone, a known PPARγ agonist, has accordingly been assessed in such a model. The C57BL/6J mouse has been chosen to evaluate the effects of the test compounds since it is prone to develop an early inflammatory response followed by fibrotic remodelling in lung after administration of bleomycin.

Mice were daily orally treated for 15 days with compound A at two different doses (30 and 100 mg/kg/day) and with rosiglitazone at 5 mg/kg/day. At the end of the treatment, animals were sacrificed and plasma samples and livers were harvested. Expression of genes that are known to be implicated in the pulmonary inflammation process was quantified and plasmatic levels of lung parameters were measured.

Bleomycin-exposed mice orally treated with vehicle for 15 days displayed a pulmonary fibrosis as shown by the statistically significant increase of lung, osteopontin, lung MCP-1 and lung TIMP-1 levels. Treatment with compound A at 30 and 100 mg/kg/day for 15 days significantly reduced levels of lung TIMP-1 compared to vehicle; levels of lung MCP-1 and osteopontin were also reduced compared to vehicle without reaching statistical significance. In contrast, when bleomycin-exposed mice were orally daily treated with rosiglitazone at 5 mg/kg/day for 15 days, lung osteopontin, lung MCP-1 and lung TIMP-1 levels increased compared to vehicle without reaching statistical significance.

MATERIALS AND METHODS

The experiments were earned out using 77 male C57B/6J mice (JANVIER LABS, C.S. 4105, Saint-Berthevin F-53941, France), weighing 20-25 g at the beginning of the experiment. The animals were housed in groups of 3-10 in polypropylene cages (floor area=1032 cm$^2$) under standard conditions: room temperature (22±2° C.), hygrometry (55±10%), light/dark cycle (12 h/12 h), air replacement (15-20 volumes/hour), water and food (SDS, RMI) ad libitum. Mice were allowed to accommodate themselves for at least 5 days prior to the experimentation. Mice were numbered by marking their tail using indelible markers.

Compound A (3 mg/mL and 10 mg/mL) and rosiglitazone (0.5 mg/mL) were formulated in 1% Methylcellulose (METOLOSE SM400, 400 Cps)+0.1% Poloxamer 188 as ready-to-use suspensions and stored at 5±3° C. during the study. 1% Methylcellulose (METOLOSE SM400, 400 Cps)+0.1% Poloxamer 188 was used as vehicle and stored at 5±30° C. during the study. Bleomycin (Laboratoire Bellon) was dissolved in 0.9% NaCl (CDM Lavoisier, France) just before use.

Dosing

Mice were allocated to the following groups:
1. 0.9% NaCl+vehicle (once a day for 15 days po), n=11,
2. 0.9% NaCl+compound A (100 mg/kg/day once a day for 15 days po), n=11,
3. 0.9% NaCl+rosiglitazone (5 mg/kg/day once a day lot 15 days po), n=11,
4. bleomycin (0.3 mg+vehicle (once a day for 15 days po), n=10,
5. bleomycin (0.3 mg)+compound A (30 mg/kg/day once a day for 15 days po), n=9,
6. bleomycin (0.3 mg)+compound A (100 mg/kg/day once a day for 15 days po), n=7,
7. bleomycin (0.3 mg)+rosiglitazone (5 mg/kg/day once a day for 15 days po), n=6.

On day 1, mice were anaesthetised with etomidate (15-20 mg/kg, ip) and then intranasally administered with bleomycin sulphate (0.3 mg (300 IU) in 0.9% NaCl (50 μL/mouse (25 μL/nostril)) or with 0.9% NaCl (50 μL/mouse (25 μL/nostril)). Mice were orally treated once a day for 15 days (day 0 to day 14) with vehicle, compound A or rosiglitazone.

Administration of vehicle, compound A or rosiglitazone on day 1 was performed 6 hours before 0.9% NaCl or bleomycin administration. The volume of administration of the test compounds was 10 mL/kg body weight for oral administrations.

Terminal Blood sampling

On day 14, 2 hours after dosing, animals were anaesthetised with pentobarbital (60 mg/kg, ip) and blood was collected using cardiac puncture. The exact time of dosing and time of sample collection were noted for each animal. Blood sampling (0.9 mL of total blood) was placed in pre-chilled 2-mL lithium-heparin collection tubes. The blood samples were gently mixed, placed on crushed ice and centrifuged within 30 min of sampling at approximately 1500×g for 10 min at approximately +4° C. For each blood sampling, the resultant plasma was separated into 2 aliquots (at least 100 µL each) and transferred using disposable plastic material into polypropylene tubes. The samples were immediately transferred in the upright position to a freezer where they were kept at −20° C.

Lung Removal

After terminal blood sampling, lung tissue was removed:
A first tissue sample (middle lobe) was harvested and fixed with paraformaldehyde, and kept at at 5±3° C.
A second tissue sample (right lobe) was frozen in liquid nitrogen and kept at −20° C.

Measured Parameters

Collagen

For the quantification of collagen, sections were stained with Picro-Sirius red and counterstained with Mayer's haematoxylin. All slides were digitized and 5 non overlapping fields of 3 different sections were randomly analysed by means of the image J software (version 1.42, N.I.H., USA). For all slides, analysis was performed by a single experimenter strictly in the same conditions.

Gene Expression mRNA extraction was performed on small frozen lung samples (50-100 mg). Briefly, samples were cryogenically ground with mortar and pestle. Samples were subsequently homogenized using marble (2×5 mn) and 1 ml of Qiazol lysis reagent (Qiagen Ref 79306) in a Retsch MM300 apparatus. RNA extraction on lung homogenates was finalized with Qiagen Rneasy lipid Kit (Ref 74804) according to the manufacturer's instructions. RNA quantity was determined with Nanodrop (ND2000 Thermo Scientific) and RNA quality was verified with Bioanalyzer (2100 Agilent Technology).

Random-primed cDNA synthesis was carried out on 100 ng total RNA using the Iscript kit (BIORAD ref 170-8891) according to the manufacturer's instructions. Real-time PCR was carried out with 7.5 ng RNA equivalents on an ABI Prism 7900 Sequence Detection System (APPLIED BIOSYSTEMS) using Iq ITaq SYBR Green Universal Rox (Ref 1725124 Biorad) and using dedicated QPCR primers. For some mRNA transcripts, quantification was performed using TaqMan probes labeled with the fluorochrome FAM and using Universal PCR MasterMix No AmpErase UNG (APPLIED BIOSYSTEMS ref 4324020). The primers and probe used for the assays are listed in the following tables:

| Target Name | Full target name | Primer names | Sequences (5'-3') |
|---|---|---|---|
| Rplp0 | ribosomal protein, large, P0 | Fw2Rplp0 PE<br>Rev2Rplp0 PE | ctgatgggcaagaacaccat (SEQ ID NO: 1)<br>gtgaggtcctccttggtgaa (SEQ ID NO: 2) |
| Tgfbr1 | transforming growth factor, beta receptor 1 | MTgfbr1FW<br>MTgfbr1REV | ggtcttgcccatcttcacat (SEQ ID NO: 13)<br>caacaggttccattttcttca (SEQ ID NO: 14) |
| Col1a1 | collagen, type 1, alpha 1 | MCol1a1FW<br>MCol1a1REV | aaaggtgctgatggttctcc (SEQ ID NO: 5)<br>gggaccgggaggaccactgg (SEQ ID NO: 6) |
| Col3a1 | collagen, type III, alpha 1 | MCol3a1FW<br>MCol3a1REV | gggatcaaatgaaggcgaat (SEQ ID NO: 15)<br>tgggtagtctcattgccttgc (SEQ ID NO: 16) |
| Spp1 (Osteopontin) | secreted pholphoprotein 1 | MSpp1FW<br>MSpp1REV | ctccaatcgtccctacagtc (SEQ ID NO: 17)<br>ggtcctcatctgtggcatca (SEQ ID NO: 18) |
| Ccl2 (MCP-1) | chemokine (C—C motif) ligand 2 | MCcl2FW<br>MCcl2REV | aggtccctgtcatgcttctg (SEQ ID NO: 11)<br>gcctactcattgggatcatc (SEQ ID NO: 12) |
| Fn1 | fibronectin 1 | MFn1FW<br>MFn1REV | gttgtctgacgctggctttaag (SEQ ID NO: 19)<br>cccacttctctccgatcttgta (SEQ ID NO: 20) |

| Target Name | Full target name | Assay ID_probe Taqman |
|---|---|---|
| Timp-1 | TIMP metallopeptidase inhibitor 1 | Mm01341361_m1 |

Real Time PGR was performed on ABI PRISM 7900 apparatus Raw data from ABI7900 were exported in text format. Analysis was performed on Excel, the relative quantity of transcript were calculated using the "Delta Delta CT method" (Livak et al. Methods 2001), using Rp1p0 as housekeeping gene for normalization and mean data from the non-treated animals (vehicle group) as reference control. Each RNA samples were reverse transcribed and quantified in triplicate.

Lung Protein Biomarkers

Protocol of Lung Proteins Extraction:

Extraction with T-PER®: Tissue Protein Extraction Reagent, prod#78510 (lot: NG174004), Thermo Scientific with: Halt Protease Inhibitor Single-Use Cocktail. EDTA-free (100×)—Prod #78425—Lot #NL178051 Thermo Fischer.

Samples of lung and supernatant were kept on ice during all experiment. For extraction, the manufacturer recommends 10 mg of tissue for 100 µl T-Per+1 µl "Halt-protease" (100×).

50 ml of T-Per buffer were prepared, to which 500 µl of "Halt-protease" (100×) were added, and the mixture was kept on ice. Samples of 50 to 70 mg of lung just thawed were weighed and cut into small pieces, and 1 ml of cold PBS was added to wash the tissue. The mixture was centrifuged at 500 g during 5 min at 4° C., and the supernatant was discarded. 100 µl/10 mg of T-Per+antiproteases (100×) were added, crushing the lung with a Potter, with 5 or 6 twists, up and down. The mixture was centrifuged at 10000 g during 5 min at 4° C. The supernatant was removed, aliquoted and kept at −20° C. for the subsequent measurement of biomarkers. Samples of 10 µl were used to dose proteins by the BCA technique, after dilution $1/10^{ème}$ in $H_2O$ mq following the procedure described in MOS: BAP-03-062-01 (Kit BCA—Pierce BCA protein assay kit—Pierce Thermo scientific, Ref: 23225).

All proteins were quantified with ELISA Kit, according to the instructions of the manufacturers:
- osteopontin: Quantikine Mouse Osteopontin immunoassay, R&D SYSTEMS®, Ref: MOST0
- MCP-1: Quantikine Mouse CCL2/JE/MCP-1 ELISA Kit, R&D SYSTEMS®, ref: MJE00
- TIMP-1: Mouse TIMP-1, R&D SYSTEMS®, Ref: TM100.

Data Processing and Statistical Analysis

All parameters were analysed using Graphpad software (version 5.1). The parameters were analysed as followed:
- Using one-way ANOVA (treatment) to compare groups (1, 2 and 3). When ANOVA was found significant, a Dunnett's test was used to compare group 1 to group 2 and to group 3.
- Using one-way ANOVA (treatment) to compare groups (1, 4, 5, 6 and 7). When ANOVA was found significant, a Dunnett's test was used to compare group 1 to group 4, to group 5, to group 6 and to group 7).

In FIGS. 17 to 27, * denotes a p-value<0.05;  denotes a p-value<0.01; * denotes a p-value<0.001.

RESULTS

1/Collagen Deposition

In bleomycin-exposed mice compound A (100 mg/kg/day) significantly decreased collagen deposition levels compared to vehicle (p<0.05). Rosiglitazone also significantly decreased collagen levels (p<0.05) (FIG. 17).

2/Lung TIMP-1

In bleomycin-exposed mice, compound A (30 and 100 mg/kg/day) significantly reduced TIMP-1 levels compared to vehicle (p<0.05) whereas rosiglitazone increased TIMP-1 levels without reaching significance (FIG. 18).

3/Lung MCP-1

In bleomycin-exposed mice, compound A (30 and 100 mg/kg/day) reduced MCP-1 levels compared to vehicle without reaching significance whereas rosiglitazone increased MCP-1 levels without reaching significance (FIG. 19).

4/Lung Osteopontin

In bleomycin-exposed mice, compound A (30 and 100 mg/kg/day) reduced osteopontin levels compared to vehicle without reaching significance whereas rosiglitazone increased osteopontin levels without reaching significance (FIG. 20).

5/TGFβR-1 Expression

In bleomycin-exposed mice, compound A (100 mg kg day) significantly inhibited TGFβR-1 expression compared to vehicle (p<0.05). Rosiglitazone also significantly inhibited TGFβ-1 expression (p<0.05) (FIG. 21).

6/Collagen Type I, Alpha I (Col1a) Expression

In bleomycin-exposed mice, compound A (100 mg/kg/day) significantly inhibited Col1a expression compared to vehicle (p<0.001) whereas rosiglitazone upregulated Col1a expression without reaching significance (FIG. 22).

7/Collagen Type III, Alpha I (Col3a) Expression

In bleomycin-exposed mice, compound A (100 mg/kg/day) significantly inhibited Col3a expression compared to vehicle (p<0.001) whereas rosiglitazone inhibited Col3a expression without reaching significance (FIG. 23).

8/TIMP-1 Expression

In bleomycin-exposed mice, compound A (30 and 100 mg/kg/day) inhibited TIMP-1 expression compared to vehicle without reaching significance whereas rosiglitazone significantly upregulated TIMP-1 expression (p<0.05) (FIG. 24).

9/MCP-1 Expression

In bleomycin-exposed mice, compound A (30 and 100 mg/kg/day) inhibited MCP-1 expression compared to vehicle without reaching significance whereas rosiglitazone upregulated TIMP-1 expression without teaching significance (FIG. 25).

10/Osteopontin Expression

In bleomycin-exposed mice, compound A (30 and 100 mg kg/day) significantly inhibited osteopontin expression compared to vehicle (p<0.05) whereas rosiglitazone had no effect on osteopontin (FIG. 26).

11/Fibronectin Expression

In bleomycin-exposed mice, compound A (100 mg/kg/day) significantly inhibited fibronectin expression compared to vehicle (p<0.05) whereas rosiglitazone upregulated fibronectin expression without reaching significance (FIG. 27).

The above results show that oral administration of compound A (30 or 100 mg/kg/day) in male C57BL/6J mice reduced the increase of inflammatory fibrotic biomarkers levels induced by bleomycin instillation in lung whereas rosiglitazone had no effect, or even a detrimental effect on these biomarkers. Taken together, these data show that compound A reduced bleomycin-induced pulmonary fibrosis in mice.

Example 4: Effect of Compound A on the Development of Bleomycin-Induced Skin Fibrosis in Mice, and Comparison with a Known PPARγ Agonist Compound A was tested in a murine model of bleomycin-induced skin fibrosis. Mice were daily orally treated for 21 days with compound A at two different doses (30 and 100 mg/kg/day) and with the PPARγ reference compound rosiglitazone at 5 mg/kg/day. At the end of the treatment, animals were sacrificed and skin samples were taken. Expression of genes that are known to be implicated in the systemic fibrosis pathway was quantified and dermal thickness and collagen content was determined.

Bleomycin-exposed mice orally treated with vehicle for 21 days displayed skin fibrosis as shown by the statistically significant increase of dermal thickness and collagen content. Treatment with compound A at 50 and 100 mg/kg/day for 21 days significantly reduced dermal thickness and collagen content compared to vehicle. A similar effect was observed in bleomycin-exposed mice orally daily treated with rosiglitazone at 5 mg/kg/day for 21 days, although the effect was less marked regarding dermal thickness.

MATERIALS AND METHODS

The experiments were carried out on 6-week-old male C56BL/6 mice (Janvier, Le Genest-Saint-Isle, France). The animals were housed in groups of 3-10 in polypropylene cages (floor area=1032 $cm^2$) under standard conditions:

room temperature (22±2° C.), hygrometry (55±10%), light/dark cycle (12 h/12 h), air replacement (15-20 volumes/hour), water and food (SDS, RM1) ad libitum. Mice were allowed to accommodate themselves for at least 5 days prior to the experimentation. Mice were numbered by marking their tail using indelible markers.

Compound A (3 mg/mL and 10 mg/mL) and rosiglitazone (0.5 mg/mL) were formulated in 1% Methylcellulose (METOLOSE SM400, 400 Cps)+0.1% Poloxamer 188 as ready-to-use suspensions and stored at 5±3° C. during the study. 1% Methylcellulose (METOLOSE SM400, 400 Cps)+0.1% Poloxamer 188 was used as vehicle and stored at 5±3° C. during the study.

Dosing

Mice were allocated to the following groups:
1. 0.9% NaCl+vehicle (once a day for 21 days po), n=7,
2. 0.9% NaCl+compound A (100 mg/kg/day once a day for 21 days po), n=8,
3. 0.9% NaCl+compound A (30 mg/kg/day once a day for 21 days po), n=8,
4. bleomycin (0.3 mg)+rosiglitazone (5 mg/kg/day once a day for 21 days po), n=8,
5. bleomycin (0.3 mg)+vehicle (once a day for 21 days po), n=6,
6. bleomycin (0.3 mg)+compound A (100 mg/kg/day once a day for 21 days po), n=7,
7. bleomycin (0.3 mg)+compound A (30 mg/kg/day once a day for 21 days po), Skin fibrosis was induced by daily injections of bleomycin (100 µL of bleomycin (Laboratoire Bellon, France) dissolved in 0.9% NaCl (CDM Lavoisier, France) at a concentration of 0.5 mg/ml, administered 6 days/week into defined areas of 1 cm² on the upper back). 0.9% NaCl was used as control (100 µL subcutaneous injections).

Mice were orally treated once a day for 21 days with vehicle, compound A or rosiglitazone. Administration of vehicle, compound A or rosiglitazone on day 1 was performed 4 hours before 0.9% NaCl or bleomycin administration.

Skin Sampling

On day 21, mice were sacrificed by cervical dislocation, and skin samples were taken and processed for analysis.

Measured Parameters:

Dermal and Adipose Layer Thickness

Lesional skin areas were excised, fixed in 4% formalin and embedded in paraffin. Five µm thick sections were stained with haematoxylin and eosin. The dermal thickness was analyzed at 100-fold magnification by measuring the distance between the epidermal-dermal junction and the dermal-subcutaneous fat junction at four sites from lesional skin of each mouse. Two independent examiners performed the evaluation before a consensus in case of more of 10% of variability of the measures.

Collagen Content of Skin

Hydroxyproline Assay

The collagen content in lesional skin samples was explored by hydroxyproline assay. After digestion of punch biopsies (Ø 3 mm) in 6M HCl for three hours at 120° C., the pH of the samples was adjusted to 7 with 6M NaOH. Afterwards, samples were mixed with 0.06 M chloramine T and incubated for 20 min at room temperature. Next, 3.15M perchloric acid and 20% p-dimethylaminobenzaldehyde were added and samples were incubated for an additional 20 min at 60° C. The absorbance was determined at 557 nm with a Spectra MAX 190 microplate spectrophotometer (Molecular Devices, Sunnyvale, Calif., USA).

Sircol Assay

Total soluble collagen in cell culture supernatants was quantified using a Sircol collagen assay (Biocolor). Briefly, cell culture supernatant was mixed with sirius red dye for 30 minutes at room temperature. After centrifugation, the pellet was dissolved in alkali reagent. Measurement was performed using a SpectraMax 190 microplate spectrophotometer (Molecular Devices) at a wavelength of 540 nm.

Data Processing and Statistical Analysis

Data were expressed as mean±standard error of the mean. The Student t-test was used for statistical analyses. A p value of less than 0.05 was considered as a statistically significant result.

In FIGS. 28 to 30 * denotes a p-value≤0.05;  denotes a p-value<0.01; * denotes a p-value<0.001.

RESULTS

Injection of bleomycin in mice resulted in an increase in dermal thickness compared to mice receiving NaCl (see FIG. 28: increase of 57% in the group bleomycin+vehicle compared to the group NaCl+vehicle). Rosiglitazone and compound A (30 mg/kg) significantly reduced dermal thickness in bleomycin-exposed mice compared to vehicle (p≤0.05). Compound A (100 mg/kg) more significantly reduced dermal thickness in bleomycin-exposed mice compared to vehicle (p<0.001).

Consistent with the reduced dermal thickening, the hydroxyproline content in lesioned skin of mice treated with compound A (30 and 100 mg/kg) and rosiglitazone was significantly lower than in lesioned skin of mice treated with vehicle, compound A (30 mg/kg) being more efficient than rosiglitazone (FIG. 29).

Compound A (30 and 100 mg/kg) and rosiglitazone also significantly reduced the collagen content compared to vehicle (FIG. 30).

Altogether these results show that compound A is efficient to prevent skin fibrosis. Compound A (100 mg/kg) even exerts better effects on dermal thickness compared to rosiglitazone.

Example 5: Activation of Human and Murine PPAR Receptors by Compound A

The ability of compound A to activate all three subtypes of PPAR receptors was determined by transient transactivation assays. These cell-based assays were carried out using Cos-7 cells transfected with a chimeric human or mouse PPARα-Gal4 receptor expression plasmid (or PPARδ-Gal4, or PPARγ-Gal4) and a 5Gal4 pGL3 TK Luc reporter plasmid. Transfections were performed by a chemical agent (Jet PEI). Transected cells were distributed in 384-wells plates and were allowed to recover for 24 h. The culture medium was then removed and fresh medium containing the compound to be tested (5 µM) was added (final concentration ranging from $10^{-4}$ M to $3 \cdot 10^{-10}$ M). After an overnight incubation, luciferase expression was measured by adding SteadyGlo according to the manufacturer's instructions (Promega). Fenofibric acid at $10^{-5}$M, GW501516 at $10^{-8}$M. and Rosiglitazone at $10^{-6}$ M were used as references. Results were expressed as percentage activity compared to references (fenofibric acid for PPARα, rosiglitazone for PPARγ, and GW501516 for PPARδ) taken as 100%. For human receptors, the results are the mean of 6 experiments, each in quadruplicate. For murine receptors, the results are the mean of 5 (PPARδ) or 6 (PPARα and γ) experiments, each in quadruplicate. Dose-effect curves and EC50 were calculated using the software Assay Explorer (MDL). The results are presented in the table below and in FIGS. 31 and 32.

|  | PPARα | | PPARγ | | PPARδ | |
|---|---|---|---|---|---|---|
|  | human | mouse | human | mouse | human | mouse |
| EC50 (μM) | 0.92 | 0.29 | 0.18 | 0.17 | 0.53 | 2* |

*estimated (plateau not reached)

These results show that compound A activates all three subtypes of PPAR receptors with an EC50 of less than 1 μM for each subtype. It can further be seen that compound A has a balanced activity between the three subtypes of PPAR receptors.

Overall, the results of examples 1-5 suggest that a good PPARδ agonist activity is required alongside with PPARα and PPARγ agonist activities in order in exert a pan-antifibrotic effect.

Example 6: Effect of Compound A on Proliferation of Lung and Dermal Fibroblasts, and Comparison with Known PPARγ and PPARα Agonists The ability of compound A to inhibit PDGF-induced lung and dermal fibroblasts proliferation was determined by performing EdU (5-ethynyl-2'-deoxyuridine) incorporation assays. These assays were carried out using primary human lung or skin fibroblasts (Promocell). The cells were plated in 96-well plates in full growth medium for 24 h, followed by 24 h starvation in serum-free medium. The medium was then replaced by fresh medium containing PDGF and compound A to be tested (at concentrations ranging from $10^{-4}$ M to 4.5 $10^{-8}$ M) for another 24 h EdU was added to the cells for the last 16 h of the compound treatment. The culture medium was then removed, the cells were fixed with formaldehyde and the EdU incorporated in the DNA of diving cells was quantified using fluorescent Click-it assay according to the manufacturer's instructions (Invitrogen). Fenofibric acid at concentrations ranging from 3 $10^{-4}$ M to 1.4 $10^{-7}$ M (PPARα) and Rosiglitazone at concentrations ranging from 3 $10^{-5}$ M to 1.4 $10^{-8}$ M (PPARγ) were used as references. Results were expressed as % of EdU-positive cells out of the total cell number. The results present the mean of biological triplicates. Dose-effect curves and IC$_{50}$ values were calculated using the GraphPad Prism software. The results are presented in the table below and in FIGS. 33 and 34.

|  | compound A | | fenofibric acid | | rosiglitazoney | |
|---|---|---|---|---|---|---|
|  | Lung | Dermal | Lung | Dermal | Lung | Dermal |
| IC$_{50}$ (μM) | 10.90 | 11.50 | NC | NC | NC | NC |

NC: not converged

Example 7: Effect of Compound A on Fibroblasts to Myofibroblasts Transition of Lung and Dermal Fibroblasts, and Comparison with Known PPARγ and PPARα Agonists The ability of compound A to inhibit TGFβ-induced lung and dermal fibroblasts to myofibroblasts transition (FMT) was determined by performing immunocytochemistry assays for the myofibroblast marker, α-smooth muscle actin (α-SMA). These assays were carried out using primary human lung or skin fibroblasts (Promocell). The cells were plated in 96-well plates in full growth medium for 24 h, followed by 24 h starvation in serum-free medium. The medium was then replaced by fresh medium containing TGFβ and compound A to be tested (at concentrations ranging from $10^{-4}$ M to 4.5 $10^{-8}$ M) for another 48 h. The culture medium was then removed, the cells were fixed with formaldehyde and stained with a primary mouse α-SMA antibody (Sigma) and secondary fluorescence-labelled goat-anti-mouse antibody (Invitrogen). α-SMA expression was quantified using Meta Xpress software. Fenofibric acid at concentrations ranging from 3 $10^{-4}$ M to 1.4 $10^{-7}$ M (PPARα) and Rosiglitazone at concentrations ranging from 3 $10^{-5}$ M to 1.4 $10^{-8}$ M (PPARγ) were used as references. Results were expressed as % of α-SMA-positive cells out of the total cell number. The data was normalised to the TGFβ treatment alone, which was taken as 100%. The results present the mean of biological triplicates.

Dose-effect curves and IC$_{50}$ values were calculated using the GraphPad Prism software. The results are presented in the table below and in FIGS. 35 and 36.

|  | compound A | | fenofibric acid | | rosiglitazone | |
|---|---|---|---|---|---|---|
|  | Lung | Dermal | Lung | Dermal | Lung | Dermal |
| IC$_{50}$ (μM) | 10.79 | ~11.18 | NC | NC | NC | NC |

NC: not converged

Altogether, these in vitro functional data demonstrate that compound A efficiently inhibits PDGF-induced proliferation and TGFβ-induced myofibroblasts transition in primary human lung and dermal fibroblasts, thus providing a link with the anti-fibrotic effects observed in vivo. In addition, these results suggest that pan-PPAR agonism might be superior to a single PPAR activation in its anti-fibrotic effects in the target cells on the two key fibrogenic pathways.

The invention claimed is:

1. A method of treating a fibrotic condition which comprises administering a therapeutically effective amount of a pan-PPAR agonist to a human subject in need thereof, wherein the pan-PPAR agonist is 5-chloro-1-[(6-benzothiazolyl)sulfonyl]-1H-indole-2-butanoic acid.

2. The method of claim 1, wherein the pan-PPAR agonist is administered orally.

3. The method of claim 2, wherein the pan-PPAR agonist is administered in the form of a pharmaceutical composition comprising one or more pharmaceutically acceptable excipients.

4. The method of claim 3, wherein the pharmaceutical composition is a tablet, a capsule or a lozenge.

5. The method of claim 3, wherein the pharmaceutical composition comprises from about 10 mg to about 1000 mg of said pan-PPAR agonist.

6. The method of claim 1, wherein the pan-PPAR agonist is administered parenterally.

7. The method of claim 6, wherein the pan-PPAR agonist is administered in the form of an aqueous solution comprising one or more pharmaceutically acceptable excipients.

8. The method of claim 1, wherein the pan-PPAR agonist is administered by inhalation.

9. The method of claim 1, wherein the pan-PPAR agonist is administered intranasally.

10. The method of claim 1, wherein the pan-PPAR agonist is administered topically.

* * * * *

SEQUENCE LISTING

```
<160> NUMBER OF SEQ ID NOS: 20

<210> SEQ ID NO 1
<211> LENGTH: 20
<212> TYPE: DNA
<213> ORGANISM: Artificial Sequence
<220> FEATURE:
<223> OTHER INFORMATION: primer
```

<400> SEQUENCE: 1
ctgatgggca agaacaccat                                    20

<210> SEQ ID NO 2
<211> LENGTH: 20
<212> TYPE: DNA
<213> ORGANISM: Artificial Sequence
<220> FEATURE:
<223> OTHER INFORMATION: primer

<400> SEQUENCE: 2
gtgaggtcct ccttggtgaa                                    20

<210> SEQ ID NO 3
<211> LENGTH: 20
<212> TYPE: DNA
<213> ORGANISM: Artificial Sequence
<220> FEATURE:
<223> OTHER INFORMATION: primer

<400> SEQUENCE: 3
accggcccTT cctgctcctc                                    20

<210> SEQ ID NO 4
<211> LENGTH: 20
<212> TYPE: DNA
<213> ORGANISM: Artificial Sequence
<220> FEATURE:
<223> OTHER INFORMATION: primer

<400> SEQUENCE: 4
gccgcacaca gcagttcttc                                    20

<210> SEQ ID NO 5
<211> LENGTH: 20
<212> TYPE: DNA
<213> ORGANISM: Artificial Sequence
<220> FEATURE:
<223> OTHER INFORMATION: primer

<400> SEQUENCE: 5
aaaggtgctg atggttctcc                                    20

<210> SEQ ID NO 6
<211> LENGTH: 20
<212> TYPE: DNA
<213> ORGANISM: Artificial Sequence
<220> FEATURE:
<223> OTHER INFORMATION: primer

<400> SEQUENCE: 6
gggaccggga ggaccactgg                                    20

<210> SEQ ID NO 7
<211> LENGTH: 22
<212> TYPE: DNA
<213> ORGANISM: Artificial Sequence
<220> FEATURE:
<223> OTHER INFORMATION: primer

<400> SEQUENCE: 7
gttgtctgac gctggcttta ag                                 22

<210> SEQ ID NO 8

```
<211> LENGTH: 22
<212> TYPE: DNA
<213> ORGANISM: Artificial Sequence
<220> FEATURE:
<223> OTHER INFORMATION: primer

<400> SEQUENCE: 8
cccacttctc tccgatcttg ta                                              22

<210> SEQ ID NO 9
<211> LENGTH: 21
<212> TYPE: DNA
<213> ORGANISM: Artificial Sequence
<220> FEATURE:
<223> OTHER INFORMATION: primer

<400> SEQUENCE: 9
cagggagtaa tggttggaat g                                               21

<210> SEQ ID NO 10
<211> LENGTH: 20
<212> TYPE: DNA
<213> ORGANISM: Artificial Sequence
<220> FEATURE:
<223> OTHER INFORMATION: primer

<400> SEQUENCE: 10
tttccatgtc gtcccagttg                                                 20

<210> SEQ ID NO 11
<211> LENGTH: 20
<212> TYPE: DNA
<213> ORGANISM: Artificial Sequence
<220> FEATURE:
<223> OTHER INFORMATION: primer

<400> SEQUENCE: 11
aggtccctgt catgcttctg                                                 20

<210> SEQ ID NO 12
<211> LENGTH: 20
<212> TYPE: DNA
<213> ORGANISM: Artificial Sequence
<220> FEATURE:
<223> OTHER INFORMATION: primer

<400> SEQUENCE: 12
gcctactcat tgggatcatc                                                 20

<210> SEQ ID NO 13
<211> LENGTH: 20
<212> TYPE: DNA
<213> ORGANISM: Artificial Sequence
<220> FEATURE:
<223> OTHER INFORMATION: primer

<400> SEQUENCE: 13
ggtcttgccc atcttcacat                                                 20

<210> SEQ ID NO 14
<211> LENGTH: 22
<212> TYPE: DNA
<213> ORGANISM: Artificial Sequence
<220> FEATURE:
<223> OTHER INFORMATION: primer

<400> SEQUENCE: 14
```
caacaggttc cattttctt ca                                             22

<210> SEQ ID NO 15
<211> LENGTH: 20
<212> TYPE: DNA
<213> ORGANISM: Artificial Sequence
<220> FEATURE:
<223> OTHER INFORMATION: primer

<400> SEQUENCE: 15
gggatcaaat gaaggcgaat                                               20

<210> SEQ ID NO 16
<211> LENGTH: 21
<212> TYPE: DNA
<213> ORGANISM: Artificial Sequence
<220> FEATURE:
<223> OTHER INFORMATION: primer

<400> SEQUENCE: 16
tgggtagtct cattgccttg c                                             21

<210> SEQ ID NO 17
<211> LENGTH: 20
<212> TYPE: DNA
<213> ORGANISM: Artificial Sequence
<220> FEATURE:
<223> OTHER INFORMATION: primer

<400> SEQUENCE: 17
ctccaatcgt ccctacagtc                                               20

<210> SEQ ID NO 18
<211> LENGTH: 20
<212> TYPE: DNA
<213> ORGANISM: Artificial Sequence
<220> FEATURE:
<223> OTHER INFORMATION: primer

<400> SEQUENCE: 18
ggtcctcatc tgtggcatca                                               20

<210> SEQ ID NO 19
<211> LENGTH: 22
<212> TYPE: DNA
<213> ORGANISM: Artificial Sequence
<220> FEATURE:
<223> OTHER INFORMATION: primer

<400> SEQUENCE: 19
gttgtctgac gctggcttta ag                                            22

<210> SEQ ID NO 20
<211> LENGTH: 22
<212> TYPE: DNA
<213> ORGANISM: Artificial Sequence
<220> FEATURE:
<223> OTHER INFORMATION: primer

<400> SEQUENCE: 20
cccacttctc tccgatcttg ta                                            22